(12) United States Patent
Cockrell et al.

(10) Patent No.: US 11,980,774 B2
(45) Date of Patent: May 14, 2024

(54) ILLUMINATION DEVICES AND RELATED METHODS FOR PHOTOTHERAPEUTIC LIGHT TREATMENTS IN THE PRESENCE OF VITAMINS

(71) Applicant: KNOW Bio, LLC, Durham, NC (US)

(72) Inventors: Adam Cockrell, Durham, NC (US); Nathan Stasko, Chapel Hill, NC (US); Jacob Kocher, Durham, NC (US)

(73) Assignee: KNOW Bio, LLC, Morrisville, NC (US)

( * ) Notice: Subject to any disclaimer, the term of this patent is extended or adjusted under 35 U.S.C. 154(b) by 120 days.

(21) Appl. No.: 17/394,764

(22) Filed: Aug. 5, 2021

(65) Prior Publication Data
US 2023/0043538 A1 Feb. 9, 2023

(51) Int. Cl.
*A61N 5/06* (2006.01)
*A61K 31/375* (2006.01)
*A61K 31/525* (2006.01)

(52) U.S. Cl.
CPC .......... *A61N 5/0624* (2013.01); *A61K 31/375* (2013.01); *A61K 31/525* (2013.01);
(Continued)

(58) Field of Classification Search
CPC .. A61N 5/06–2005/073; A61K 31/375; A61K 31/525; A61L 2/00–2/28
See application file for complete search history.

(56) References Cited

U.S. PATENT DOCUMENTS 8,240,312 B2 8/2012 Feuerstein et al.
8,435,273 B2 5/2013 Lum et al.
(Continued)

FOREIGN PATENT DOCUMENTS

DE 102010010763 A1 9/2011
WO 2013028833 A1 2/2013

OTHER PUBLICATIONS

Keil, Shawn, et al., "Inactivation of Middle East respiratory syndrome coronavirus (MERS-CoV) in plasma products using a riboflavin-based and ultraviolet light-based photochemical treatment," Transfusion, vol. 56, Dec. 2016, AABB, pp. 2948-2952.
(Continued)

*Primary Examiner* — Jonathan T Kuo
(74) *Attorney, Agent, or Firm* — Withrow & Terranova, P.L.L.C.

(57) ABSTRACT

Devices and related methods for impinging light on tissue to induce one or more biological effects, and more particularly illumination devices and related methods for phototherapeutic light treatments in the presence of vitamins are disclosed. Biological effects may include at least one of inactivating and inhibiting growth of one or more combinations of microorganisms and pathogens, including but not limited to viruses. Phototherapeutic light treatments in the presence of vitamins may involve providing one or more vitamins in the form of a coating or film on a surface of a target tissue and irradiating the target tissue with light. By performing the phototherapeutic light treatment in the presence of vitamins, efficacy of the light treatment may be improved, thereby reducing viral loads and/or reducing doses of light received by the target tissue.

21 Claims, 11 Drawing Sheets

(52) U.S. Cl.
CPC ...... *A61N 2005/063* (2013.01); *A61N 2005/0659* (2013.01); *A61N 2005/0661* (2013.01); *A61N 2005/0662* (2013.01)

(56) References Cited

U.S. PATENT DOCUMENTS

| | | | |
|---|---|---|---|
| 8,838,228 B2 | 9/2014 | Beisang, III et al. | |
| 9,023,092 B2* | 5/2015 | Natale | A61N 5/0624 606/9 |
| 9,486,284 B2* | 11/2016 | Depfenhart | A61B 18/203 |
| 9,901,747 B2 | 2/2018 | Gamelin et al. | |
| 10,639,498 B2 | 5/2020 | Enwemeka et al. | |
| 10,780,189 B2 | 9/2020 | Randers-Pehrson et al. | |
| 10,981,017 B2 | 4/2021 | Enwemeka et al. | |
| 11,266,855 B2* | 3/2022 | Enwemeka | A61N 5/0603 |
| 11,318,325 B2 | 5/2022 | Rezaie et al. | |
| 2004/0193236 A1 | 9/2004 | Altshuler et al. | |
| 2008/0255498 A1 | 10/2008 | Houle | |
| 2009/0143842 A1* | 6/2009 | Cumbie | A61N 5/0624 600/365 |
| 2013/0023966 A1* | 1/2013 | Depfenhart | A61B 18/203 607/89 |
| 2013/0274549 A1* | 10/2013 | Natale | A61B 1/015 600/104 |
| 2019/0126057 A1* | 5/2019 | Feldreich | A61N 5/062 |
| 2020/0222718 A1* | 7/2020 | Enwemeka | A61L 2/0076 |
| 2021/0052760 A1 | 2/2021 | Bouschbacher et al. | |
| 2021/0187315 A1 | 6/2021 | Murdeshwar et al. | |
| 2021/0196977 A1 | 7/2021 | Zhang | |
| 2021/0346500 A1 | 11/2021 | Schikora | |
| 2021/0402212 A1 | 12/2021 | Schupp et al. | |
| 2022/0088409 A1 | 3/2022 | Dombrowksi et al. | |

OTHER PUBLICATIONS

Keil, Shawn, et al., "Inactivation of viruses in platelet and plasma products using a riboflavin-and-UV-based photochemical treatment," Transfusion, vol. 55, Jul. 2015, AABB, pp. 1736-1744.

Ragan, Izabela, et al., "Pathogen reduction of SARS-CoV-2 virus in plasma and whole blood using riboflavin and UV light," PLOS One, May 29, 2020, 11 pages.

Thomas, Suma, et al., "Effect of High-Dose Zinc and Ascorbic Acid Supplementation vs. Usual Care on Symptom Length and Reduction Among Ambulatory Patients With SARS-CoV-2 Infection," JAMA Network Open, vol. 4, Issue 2, Feb. 12, 2021, 10 pages.

International Search Report and Written Opinion for International Patent Application No. PCT/US2022/074364, dated May 30, 2023, 14 pages.

* cited by examiner

MERS-CoV

FIG. 4A

- □ 1μM RFN + 1μM AA
- ○ 1μM RFN + 0.1μM AA
- △ 1μM RFN + 0μM AA

FIG. 4B

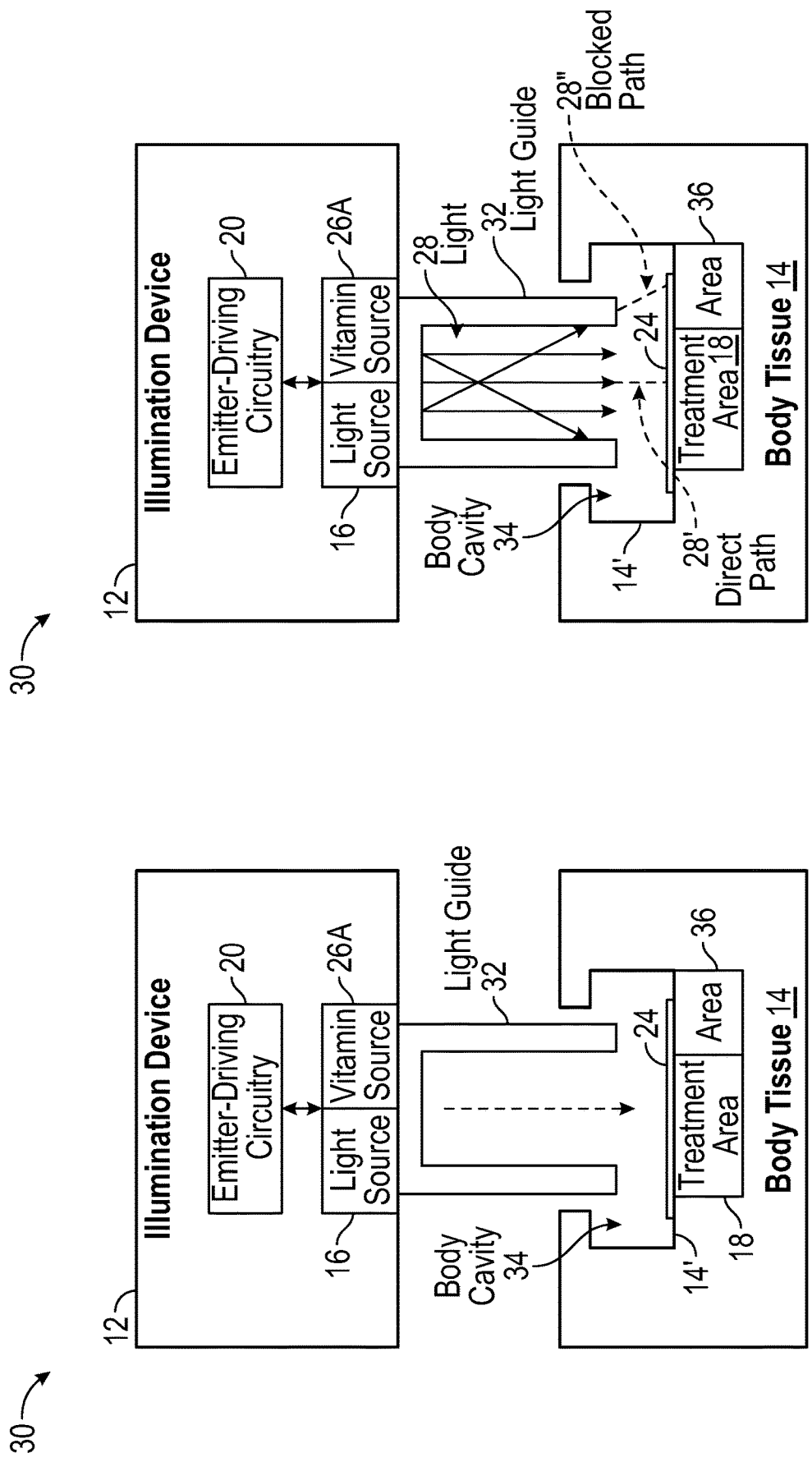

ILLUMINATION DEVICES AND RELATED METHODS FOR PHOTOTHERAPEUTIC LIGHT TREATMENTS IN THE PRESENCE OF VITAMINS

FIELD OF THE DISCLOSURE

The present disclosure relates generally to devices and methods for impinging light on tissue to induce one or more biological effects, and more particularly to illumination devices and related methods for phototherapeutic light treatments in the presence of vitamins.

BACKGROUND

Microorganisms, including disease-causing pathogens, can typically invade tissues of the human body via mucosal surfaces within body cavities, such as mucous membranes or mucosae of the respiratory tract. A number of respiratory diseases and infections, including viral and bacterial, can be attributed to such disease-causing pathogens. Examples include Orthomyxoviridae (e.g., influenza), common colds, coronaviridae (e.g., coronavirus), picornavirus infections, tuberculosis, pneumonia, bronchitis, and sinusitis. Most respiratory tract infections begin when a subject is exposed to pathogen particles, which can enter the body through the mouth and nose. For viral infections, cells at the site of infection must be accessible, susceptible, and permissive for virus infection and replication, and local host anti-viral defense systems must be absent or initially ineffective. Conventional treatments for infections typically involve systemic administration of antimicrobials, such as antibiotics for bacterial infections, that can sometimes lead to drug resistance and in some instances gastro-intestinal distress. Other conventional treatment protocols may involve managing and enduring symptoms while waiting for infections to clear, particularly for viral infections.

Upper respiratory tract infections, including the common cold, influenza, and those resulting from exposure to coronaviridae are widely prevalent infections that continually impact the worldwide population. In some instances, upper respiratory tract infections can progress to cause serious and sometimes fatal diseases that develop in the lower respiratory tract or elsewhere in the body. The art continues to seek improved treatment options for upper respiratory tract conditions that are capable of overcoming challenges associated with conventional treatment options.

SUMMARY

The present disclosure relates generally to devices and methods for impinging light on tissue to induce one or more biological effects, and more particularly to illumination devices and related methods for phototherapeutic light treatments in the presence of vitamins. Biological effects may include at least one of inactivating and inhibiting growth of one or more combinations of microorganisms and pathogens, including but not limited to viruses. Phototherapeutic light treatments in the presence of vitamins may involve providing one or more vitamins in the form of a coating or film on a surface of a target tissue and irradiating the target tissue with light. By performing the phototherapeutic light treatment in the presence of vitamins, efficacy of the light treatment may be improved, thereby reducing viral loads and/or reducing doses of light received by the target tissue.

In one aspect, a method comprises: providing a topical coating to a surface of mammalian tissue, the topical coating comprising at least one vitamin; providing a light source configured to emit light; and irradiating the surface of the mammalian tissue with the light to induce a biological effect. In certain embodiments, the at least one vitamin comprises a source of riboflavin, or a source of riboflavin and a source of ascorbate. In certain embodiments, providing the topical coating comprises applying a solution to the surface of the mammalian tissue, wherein the solution comprises the at least one vitamin. In certain embodiments, providing the topical coating comprises chewing and swallowing an oral dose of the at least one vitamin. The topical coating may comprise a mixture of a bodily fluid and the at least one vitamin. In certain embodiments, the bodily fluid may comprise saliva or mucus. The light source may be configured to emit light with a peak wavelength in a range from 315 nanometers (nm) to 600 nm, or in a range from 400 nm to 450 nm. In certain embodiments, the light source is configured to emit light with a first peak wavelength in a range from 315 nm to 600 nm and a second peak wavelength in a range from 600 nm to 1600 nm, wherein the first peak wavelength is different than the second peak wavelength. In certain embodiments, the biological effect comprises altering a concentration of one or more pathogens and altering growth of the one or more pathogens. The one or more pathogens may comprise an enveloped virus, such as coronaviridae and/or influenza.

In another aspect, an illumination device comprises: at least one light source configured to irradiate light on mammalian tissue; driver circuitry configured to drive the at least one light source; and a vitamin source configured to provide at least one vitamin to the mammalian tissue. In certain embodiments, the illumination device further comprises a light guide that is optically coupled to the at least one light source. The mammalian tissue may reside within a body cavity and the light guide may be configured to be at least partially inserted within the body cavity. In certain embodiments, the light guide comprises a rigid material. In certain embodiments, the light guide comprises a flexible material that is configured to conform to at least a portion of the body cavity. In certain embodiments, the light guide comprises a hollow core and the vitamin source is arranged to provide the at least one vitamin through the hollow core. The at least one light source may be configured to emit light with a peak wavelength in a range from 315 nm to 600 nm, or in a range from 400 nm to 450 nm. In certain embodiments, the at least one light source is configured to emit light with a first peak wavelength in a range from 315 nm to 600 nm and a second peak wavelength in a range from 600 nm to 1600 nm, wherein the first peak wavelength is different than the second peak wavelength.

In another aspect, any of the foregoing aspects individually or together, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

FIG. 2 is a chart illustrating light inhibition of SARS-CoV-2 in the presence of one or more vitamins according to principles of the present disclosure.

FIG. 3A is a chart illustrating light treatments on the South African variant of SARS-CoV-2 (SARS-CoV-2 SA) samples where various amounts of ascorbate and a constant amount of riboflavin were diluted in a same type of artificial saliva and added to the SARS-CoV-2 SA samples.

FIG. 4A is a chart illustrating an experimental control where light treatments were applied to MERS-CoV samples in media and in the absence of any vitamins.

FIG. 4B is a chart illustrating light treatments on MERS-CoV samples where various amounts of ascorbate and 1 micromolar ($\mu M$) of riboflavin were diluted in a same type of artificial saliva and added to the MERS-CoV samples.

FIG. 8A is an illustration of an exemplary configuration of an illumination device that includes a light guide for delivering light to a body tissue in the presence of one or more vitamins to induce at least one biological effect.

FIG. 8B is an illustration of the exemplary configuration of FIG. 8A showing delivery of the light to the body tissue after a topical coating that includes the one or more vitamins is applied to the body tissue.

DETAILED DESCRIPTION

Figure 1A:
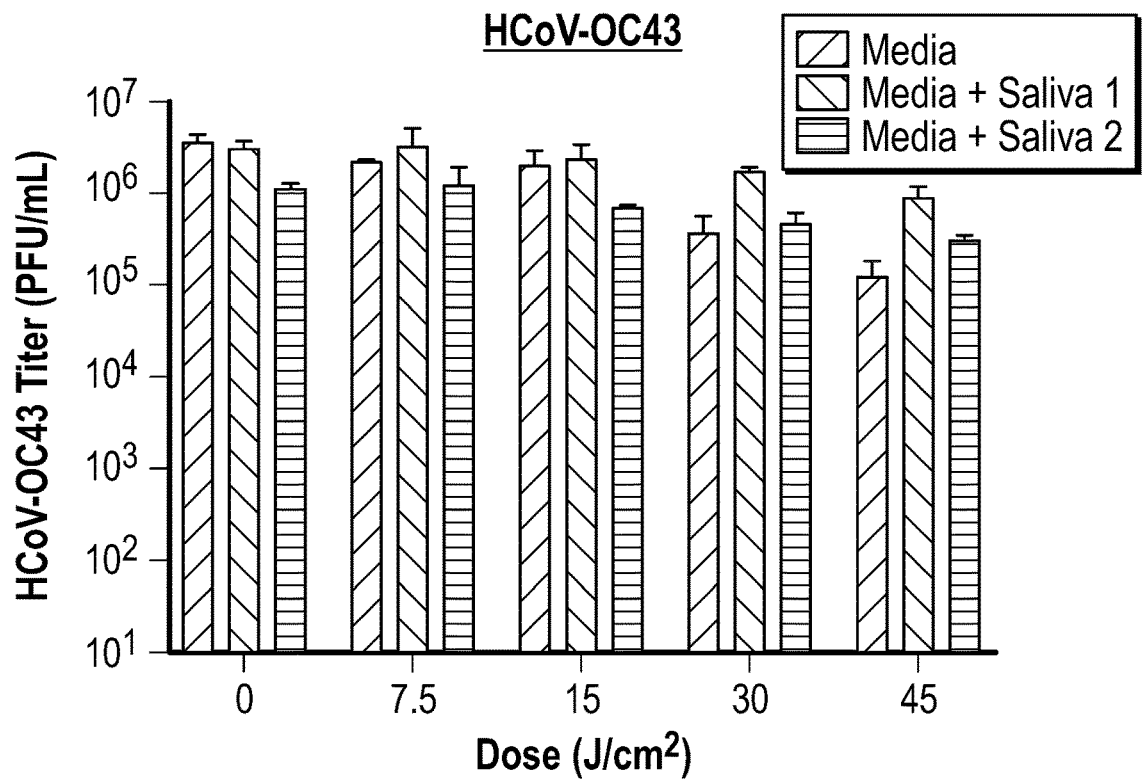
FIG. 1A is a chart illustrating an experimental control where light treatments were applied to human coronavirus OC43 (HCoV-OC43) samples in the absence of any vitamins.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Embodiments are described herein with reference to schematic illustrations of embodiments of the disclosure. As such, the actual dimensions of the layers and elements can be different, and variations from the shapes of the illustrations as a result, for example, of manufacturing techniques and/or tolerances, are expected. For example, a region illustrated or described as square or rectangular can have rounded or curved features, and regions shown as straight lines may have some irregularity. Thus, the regions illustrated in the figures are schematic and their shapes are not intended to illustrate the precise shape of a region of a device and are not intended to limit the scope of the disclosure. Additionally, sizes of structures or regions may be exaggerated relative to other structures or regions for illustrative purposes and, thus, are provided to illustrate the general structures of the present subject matter and may or may not be drawn to scale. Common elements between figures may be shown herein with common element numbers and may not be subsequently re-described.

The present disclosure relates generally to devices and related methods for impinging light on tissue to induce one or more biological effects, and more particularly to illumination devices and related methods for phototherapeutic light treatments in the presence of vitamins. Biological effects may include at least one of inactivating and inhibiting growth of one or more combinations of microorganisms and pathogens, including but not limited to viruses. Phototherapeutic light treatments in the presence of vitamins may involve providing one or more vitamins in the form of a coating or film on a surface of a target tissue and irradiating the target tissue with light. By performing the phototherapeutic light treatment in the presence of vitamins, efficacy of the light treatment may be improved, thereby reducing viral loads and/or reducing doses of light received by the target tissue.

Aspects of the present disclosure relate to devices and methods for impinging light on a mammalian tissue in the presence of one or more vitamins. In certain aspects, the mammalian tissue may be provided within a body and/or a body cavity of a mammal, where the light may include at least one characteristic that exerts or induces at least one biological effect within or on the tissue. Exemplary tissues include those of the upper and/or lower respiratory tract, including tissues and cavities that are accessible via the oral cavity and/or intranasal passageways. The principles of the present disclosure may also be applicable to other mammalian tissues and body cavities, including the skin and the ear canal, among others.

Biological effects may include at least one of inactivating and inhibiting growth of one or more combinations of microorganisms and pathogens, including but not limited to viruses, bacteria, fungi, and other microbes, among others. Biological effects may also include one or more of upregulating and/or downregulating a local immune response, stimulating enzymatic generation of nitric oxide to increase endogenous stores of nitric oxide, releasing nitric oxide from endogenous stores of nitric oxide, and inducing an anti-inflammatory effect. Wavelengths of light and particular vitamins or combinations of vitamins may be selected based on at least one intended biological effect for one or more of the targeted tissues and the targeted microorganisms and/or pathogens. In certain aspects, wavelengths of light may include visible light in any number of wavelength ranges based on the intended biological effect. Further aspects involve light impingement on tissue in the presence of one or more vitamins for multiple microorganisms and/or multiple pathogenic biological effects, either with light of a single peak wavelength or a combination of light with more than one peak wavelength. Devices and methods for light treatments are disclosed that provide light doses for inducing biological effects on various targeted pathogens and targeted tissues with increased efficacy and reduced cytotoxicity. Light doses may include various combinations of irradiances, wavelengths, and exposure times, and such light doses may be administered continuously or discontinuously with a number of pulsed exposures.

Aspects of the present disclosure relate to devices and methods for treating, preventing, and/or reducing the biological activity of pathogens while they are in one or more areas of the upper respiratory tract and hopefully before they travel to the lungs or elsewhere in the body. In certain aspects, devices and methods as disclosed herein may prevent or reduce infections by reducing microbial load, decreasing the ability for penetration into cells at the site of infection, and amplifying host defense systems, all of which may minimize or avoid the need for traditional antimicrobial medicines. In further aspects, devices and methods for light irradiation of tissues in the presence of one or more vitamins as disclosed herein may be provided to supplement and/or enhance the effects of traditional antimicrobial medicines.

The present disclosure is generally directed to illumination devices, apparatus, and methods for impinging light onto living tissue in the presence of one or more vitamins in order to induce one or more therapeutic biological effects. In various aspects, induced biological effects may include at least one of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect. In certain aspects, the light may be referred to as nitric oxide modulating light to increase concentrations of unbound nitric oxide within living tissue. Embodiments of the present disclosure may administer light at one or more wavelengths in the presence of one or more vitamins as a pre-exposure prophylaxis or a post-exposure prophylaxis in order to eliminate pathogens in or on tissue of the upper respiratory tract and/or amplify host defense systems. Embodiments of the present disclosure may be used to prevent and/or treat respiratory infections and other infectious diseases. For example, in certain embodiments, a hand-held illumination device may administer light at one or more wavelengths and in the presence of one or more vitamins as a prophylactic measure to counteract invading viral pathogens and corresponding diseases that may originate in the respiratory tract.

In a specific example, light treatments with one or more topically applied vitamins may be administered that reduces viral infectivity and incidence of COVID-19 in individuals who have been infected or believe they may have been exposed to SARS-CoV-2 virus. In various examples, light treatments with one or more topically applied vitamins may be administered that reduce viral infectivity and incidence of other pathogens and corresponding diseases, such as human coronavirus OC43 and/or certain strains of influenza. In certain aspects, illumination devices of the present disclosure may be provided or referred to as phototherapeutic and/or phototherapy devices.

The term "phototherapy" relates to the therapeutic use of light. As used herein, phototherapy may be used to treat and/or prevent microbial infections. The mechanisms by which certain wavelengths of light are effective can vary, depending on the wavelength that is administered and the targeted microorganisms and/or pathogens. Biological effects, including antimicrobial effects, can be provided over a wide range of wavelengths, including ultraviolet (UV) ranges, visible light ranges, and infrared ranges, and combinations thereof.

The term "peak wavelength" is generally used herein to refer to the wavelength that is of the greatest radiometric power of the light emitted by a light emitter. The term "dominant wavelength" may refer to the perceived color of a spectrum, i.e., the single wavelength of light which produces a color sensation most similar to the color sensation perceived from viewing light emitted by the light source (i.e., it is roughly akin to "hue"), as opposed to "peak wavelength", which refers to the spectral line with the greatest power in the spectral power distribution of the light source. Because the human eye does not perceive all wavelengths equally (e.g., it perceives yellow and green light better than red and blue light), and because the light emitted by many solid state light emitters (e.g., LEDs) is actually a range of wavelengths, the color perceived (i.e., the dominant wavelength) is not necessarily equal to (and often differs from) the wavelength with the highest power (peak wavelength). A truly monochromatic light such as a laser may have the same dominant and peak wavelengths. For the purposes of this disclosure, unless otherwise specified herein, wavelength values are discussed as peak wavelength values.

Various wavelengths of visible light may be irradiated on human tissue with little or no impact on tissue viability. In certain embodiments, various wavelengths of visible light may elicit antimicrobial and/or anti-pathogenic behavior in tissue of the respiratory tract, including any of the aforementioned biological effects. For example, light with a peak wavelength in a range from 400 nanometers (nm) to 450 nm may inactivate microorganisms that are in a cell-free environment and/or inhibit replication of microorganisms that are in a cell-associated environment and/or stimulate enzymatic generation of nitric oxide, while also upregulating a local immune response in target tissue. In this regard, light with a peak wavelength in a range from 400 nm to 450 nm may be well suited for fighting invading viral pathogens and corresponding diseases that may originate in the respiratory tract, including Orthomyxoviridae (e.g., influenza), common colds, coronaviridae (e.g., coronavirus), picornavirus infections, tuberculosis, pneumonia, bronchitis, and sinusitis. Depending on the pathogen and corresponding disease, light with a peak wavelength in a range from 315 nm to 600 nm, or in a range from 315 nm to 500 nm, or in a range from 315 nm to 450 nm may also be used. In certain embodiments, red or near-infrared (NIR) light (e.g., peak wavelength range from 600 nm to 1600 nm) may be useful to provide anti-inflammatory effects and/or to promote vasodilation. Anti-inflammatory effects may be useful in treating disorders, particularly microbial disorders that result in inflammation along the respiratory tract. In this regard, red and/or NIR light may be used as part of treatment protocols that reduce any tissue inflammation that may result from exposure to blue light, which may positively impact cell viability, thereby lowering cytotoxicity even further. A decrease in inflammation can be beneficial when treating viral infections, particularly when a virus can elicit a cytokine storm and/or inflammation can result in secondary bacterial infections. Accordingly, the combination of blue light, such as light at around 425 nm, and red light at one or more anti-inflammatory wavelengths, can provide a desirable combination of biological effects.

Depending on the application, other wavelength ranges of light may also be administered to human tissue. For example, UV light (e.g., UV-A light having a peak wavelength in a range of from 315 nm to 400 nm, UV-B light having a peak wavelength in a range of from 280 nm to 315 nm, and UV-C light having a peak wavelength in a range from 200 nm to 280 nm) may be effective for inactivating microorganisms that are in a cell-free environment and/or inhibit replication of microorganisms that are in a cell-associated environment and/or stimulate enzymatic generation of nitric oxide. However, overexposure to UV light may lead to cytotoxicity concerns in associated tissue. It may therefore be desirable to use shorter cycles and/or lower doses of UV light than corresponding treatments with only visible light.

An illumination device for the treatment of pathogens and/or for inducing one or more biological effects may take any form suitable for delivering light to the target tissue. The device may contain a light source capable of emitting a suitable light spectrum that can provide one or more direct or indirect biological effects. A light spectrum can be represented with a graph of emission intensity versus wavelength of light for any particular light source. In certain aspects, light sources may be provided with light characteristics in the visible spectrum, for example with light emissions with peak wavelengths primarily in a range from 400 nm to 700 nm. Depending on the target application, light characteristics may also include infrared or near-infrared peak wavelengths at or above 700 nm, or UV peak wavelengths at or below 400 nm as described above. As used herein, light may include visual and non-visual electromagnetic radiation with single or multiple peak wavelengths in a range from 180 nm to 4000 nm. In certain embodiments, light emissions may have a single peak wavelength in a range from 200 nm to 1,000 nm, or in a range from 315 nm to 600 nm, or in a range from 400 nm to 490 nm, or in a range from 400 nm to 435 nm, or in a range from 400 nm to 420 nm, or in a range from 400 nm to 440 nm, or in a range from 400 nm to 450 nm, or in a range from 420 nm to 440 nm, or in a range from 450 nm to 490 nm, or in a range from 500 nm to 900 nm, or in a range from 490 nm to 570 nm, or in a range from 510 nm to 550 nm, or in a range from 520 nm to 540 nm, or in a range from 525 nm to 535 nm, or in a range from 528 nm to 532 nm, or in from 630 nm to 670 nm, or in a range from 320 nm to 400 nm, or in a range from 385 nm to 450 nm, or in a range from 350 nm to 395 nm, or in a range from 280 nm to 320 nm, or in a range from 320 nm to 350 nm, or in a range from 200 nm to 280 nm, or in a range from 260 nm to 270 nm, or in a range from 240 nm to 250 nm, or in a range from 200 nm to 225 nm. In further embodiments, light emissions may include multiple peak wavelengths selected from any of the above listed ranges, depending on the target application and desired biological effects. Depending on the target application, full width half maximum (FWHM) values for any of the above-described peak wavelength ranges may be less than or equal to 100 nm, or less than or equal to 90 nm, or less than or equal to 40 nm, or less than or equal to 20 nm. In certain aspects, lower FWHM values are typically associated with single emission color light-emitting diodes (LEDs) in any of the above-described wavelength bands. Larger FWHM values (e.g., from 40 nm to 100 nm) may be associated with phosphor-converted LEDs where spectral bandwidths are a combination of LED emissions and phosphor-converted emissions. Exemplary phosphor-converted LEDs that may be applicable to the present disclosure are phosphor-converted amber LEDs having peak wavelengths in a range from 585 nm to 600 nm and FWHM values in a range from 70 nm to 100 nm, and phosphor-converted mint and/or lime LEDs having peak wavelengths in a range from 520 nm to 560 nm. Additional embodiments of the present disclosure may also be applicable to broad spectrum white LEDs that may include an LED with a peak wavelength in a range from 400 nm to 470 nm, and one or more phosphors to provide the broad emission spectrum. In such embodiments, a broad spectrum LED may provide certain wavelengths that induce one or more biological effects while also providing broad spectrum emissions to the target area for illumination. In this regard, light impingement on tissue for single and/or multiple microorganisms and/or multiple pathogenic biological effects may be provided with light of a single peak wavelength or a combination of light with more than one peak wavelength.

Doses of light to induce one or more biological effects may be administered with one or more light characteristics, including peak wavelengths, radiant flux, and irradiance to target tissues. Irradiances to target tissues may be provided in a range from 0.1 milliwatts per square centimeter (mW/cm$^2$) to 200 mW/cm$^2$, or in a range from 5 mW/cm$^2$ to 200 mW/cm$^2$, or in a range from 5 mW/cm$^2$ to 100 mW/cm$^2$, or in a range from 5 mW/cm$^2$ to 60 mW/cm$^2$, or in a range from 60 mW/cm$^2$ to 100 mW/cm$^2$, or in a range from 100 mW/cm$^2$ to 200 mW/cm$^2$. Such irradiance ranges may be administered in one or more of continuous wave and pulsed configurations, including LED-based photonic devices that are configured with suitable power (radiant flux) to irradiate a target tissue with any of the above-described ranges. A light source for providing such irradiance ranges may be configured to provide radiant flux values from the light source of at least 5 mW, or at least 10 mW, or at least 15 mW, or at least 20 mW, or at least 30 mW, or at least 40 mW, or at least 50 mW, or at least 100 mW, or at least 200 mW, or in a range of from 5 mW to 200 mW, or in a range of from 5 mW to 100 mW, or in a range of from 5 mW to 60 mW, or in a range of from 5 mW to 30 mW, or in a range of from 5 mW to 20 mW, or in a range of from 5 mW to 10 mW, or in a range of from 10 mW to 60 mW, or in a range of from 20 mW to 60 mW, or in a range of from 30 mW to 60 mW, or in a range of from 40 mW to 60 mW, or in a range of from 60 mW to 100 mW, or in a range of from 100 mW to 200 mW, or in a range of from 200 mW to 500 mW, or in another range specified herein. Depending on the configuration of one or more of the light sources, the corresponding illumination device, and the distance away from a target tissue, the radiant flux value for the light source may be higher than the irradiance value at the tissue.

While certain peak wavelengths for certain target tissue types may be administered with irradiances up to 1 W/cm$^2$ without causing significant tissue damage, safety considerations for other peak wavelengths and corresponding tissue types may require lower irradiances, particularly in continuous wave applications. In certain embodiments, pulsed irradiances of light may be administered, thereby allowing safe application of significantly higher irradiances. Pulsed irradiances may be characterized as average irradiances that fall within safe ranges, thereby providing no or minimal damage to the applied tissue. In certain embodiments, irradiances in a range from 0.1 W/cm$^2$ to 10 W/cm$^2$ may be safely pulsed to target tissue.

Administered doses of light, or light doses, may be referred to as therapeutic doses of light in certain aspects. Doses of light may include various suitable combinations of the peak wavelength, the irradiance to the target tissue, and the exposure time period. Particular doses of light are disclosed that are tailored to provide safe and effective light for inducing one or more biological effects for various types of pathogens and corresponding tissue types. In certain aspects, the dose of light may be administered within a single time period in a continuous or a pulsed manner. In further aspects, a dose of light may be repeatably administered over a number of times to provide a cumulative or total dose over a cumulative time period. By way of example, a single dose of light as disclosed herein may be provided over a single time period, such as in a range from 10 microseconds to no more than an hour, or in a range from 10 seconds to no more than an hour, while the single dose may be repeated at least twice to provide a cumulative dose over a cumulative time period, such as a 24-hour time period. In certain embodiments, doses of light are described that may be provided in a range from 0.5 joules per square centimeter (J/cm$^2$) to 100 J/cm$^2$, or in a range from 0.5 J/cm$^2$ to 50 J/cm$^2$, or in a range from 2 J/cm$^2$ to 80 J/cm$^2$, or in a range from 5 J/cm$^2$ to 50 J/cm$^2$, while corresponding cumulative doses may be provided in a range from 1 J/cm$^2$ to 1000 J/cm$^2$, or in a range from 1 J/cm$^2$ to 500 J/cm$^2$, or in a range from 1 J/cm$^2$ to 200 J/cm$^2$, or in a range from 1 J/cm$^2$ to 100 J/cm$^2$, or in a range from 4 J/cm$^2$ to 160 J/cm$^2$, or in a range from 10 J/cm$^2$ to 100 J/cm$^2$, among other disclosed ranges. In a specific example, a single dose may be administered in a range from 10 J/cm$^2$ to 20 J/cm$^2$, and the single dose may be repeated twice a day for four consecutive days to provide a cumulative dose in a range from 80 J/cm$^2$ to 160 J/cm$^2$. In another specific example, a single dose may be administered at about 30 J/cm$^2$, and the single dose may be repeated twice a day for seven consecutive days to provide a cumulative dose of 420 J/cm$^2$.

In still further aspects, light for inducing one or more biological effects may include administering different doses of light to a target tissue in the presence of one or more vitamins to induce one or more biological effects for different target pathogens. As disclosed herein, a biological effect may include altering a concentration of one or more pathogens within the body and altering growth of the one or more pathogens within the body. The biological effect may include at least one of inactivating a first pathogen in a cell-free environment, inhibiting replication of the first pathogen in a cell-associated environment, upregulating a local immune response in mammalian tissue, stimulating enzymatic generation of nitric oxide to increase endogenous stores of nitric oxide in the mammalian tissue, releasing nitric oxide from endogenous stores of nitric oxide in the mammalian tissue, and inducing an anti-inflammatory effect in the mammalian tissue. As further disclosed herein, a pathogen may include a virus, a bacteria, and a fungus, or other any other types of microorganisms that can cause infections. Notably, light doses as disclosed herein may provide non-systemic and durable effects to targeted tissues. Light can be applied locally and without off-target tissue effects or overall systemic effects associated with conventional drug therapies which can spread throughout the body. In this regard, phototherapy may induce a biological effect and/or response in a target tissue without triggering the same or other biological responses in other parts of the body. Phototherapy as described herein may be administered with safe and effective doses that are durable. For example, a dose may be applied for minutes at a time, one to a few times a day, and the beneficial effect of the phototherapy may continue in between treatments.

Light sources may include one or more of LEDs, organic LEDs (OLEDs), lasers and other lamps according to aspects of the present disclosure. Lasers may be used for irradiation in combination with optical fibers or other delivery mechanisms. LEDs are solid state electronic devices capable of emitting light when electrically activated. LEDs may be configured across many different targeted emission spectrum bands with high efficiency and relatively low costs. Accordingly, LEDs may be used as light sources in photonic devices for phototherapy applications. Light from an LED is administered using a device capable of delivering the requisite power to a targeted treatment area or tissue. High power LED-based devices can be employed to fulfill various spectral and power needs for a variety of different medical applications. LED-based photonic devices described herein may be configured with suitable power to provide irradiances as high as 100 mW/cm$^2$ or 200 mW/cm$^2$ in the desired wavelength range. An LED array in this device can be incorporated into an irradiation head, hand piece and/or as an external unit.

In addition to various sources of light, the principles of the present disclosure are also applicable to one or more other types of directed energy sources. As used herein, a directed energy source may include any of the various light sources previously described, and/or an energy source capable of providing one or more of heat, IR heating, resistance heating, radio waves, microwaves, soundwaves, ultrasound waves, electromagnetic interference, and electromagnetic radiation that may be directed to a target body tissue. Combinations of visual and non-visual electromagnetic radiation may include peak wavelengths in a range from 180 nm to 4000 nm. Illumination devices as disclosed herein may include a light source and another directed energy source capable of providing directed energy beyond visible and UV light. In other embodiments, the other directed energy source capable of providing directed energy beyond visible and UV light may be provided separately from illumination devices of the present disclosure.

Aspects of the present disclosure relate to various combinations of light irradiation to target tissue in the presence of one or more vitamins. The one or more vitamins may be provided in the form of a topical coating or film on a surface of a target tissue that is irradiated. The topical coating may include saliva for oral applications. For example, the one or more vitamins may be provided in the form of a solution that is sprayed, swallowed, or otherwise applied to form a topical coating on the target tissue, such as the throat and/or oropharynx of a user. In other embodiments, the one or more vitamins may be provided in the form of an oral dose that may be chewed and swallowed, such as a chewable tablet or a gelatin-based chewable material. The topical coating may include other bodily fluids, depending on the location of the target tissue, such as mucus for one or more portions along the upper respiratory tract. As will be described below in greater detail, different vitamins may be provided with different doses and/or wavelengths of light to target various viruses. According to the present disclosure, certain vitamins, such as riboflavin (e.g., vitamin B$_2$) by itself or in combination with ascorbic acid or ascorbate (e.g., vitamin C), may enhance light treatment mechanisms, thereby providing increased efficacy and/or the ability to reduce doses of light that are irradiated to corresponding tissue.

FIGS. 1A to 5B are charts illustrating light inhibition of viruses in the presence of one or more vitamins according to the present disclosure. The disclosed principles were demonstrated in the context of human coronavirus OC43 (HCoV-OC43), SARS-CoV-2, human rhinovirus, and influenza A and B virus samples provided in a cell media. The selected vitamin sources included certain sources of riboflavin and ascorbate, although any vitamin sources for riboflavin and vitamin C may be used without deviating from the disclosed principles. The riboflavin source comprised riboflavin-5'-phosphate or riboflavin-5'-monophosphate, although other derivatives of riboflavin may also be employed. The vitamin sources were diluted in artificial saliva, added to the various virus samples, and then the resulting samples were exposed to light with a peak wavelength of 425 nm at a variety of doses. After exposure to the light, the titer of the virus stock in each sample was assayed for the virus titer and expressed in plaque-forming units per milliliter (PFU/mL).

FIGS. 1A to 1D are provided in the context of HCoV-OC43, which is generally known as one of the viruses associated with the common cold. FIG. 1A is a chart illustrating an experimental control where light treatments were applied to HCoV-OC43 samples in the absence of any vitamins. Three HCoV-OC43 samples were subjected to 425 nm light at doses up to 45 J/cm$^2$. A first sample included HCoV-OC43 in only its corresponding media, and the other two samples further included different artificial saliva sources (labeled as Saliva 1 and Saliva 2 in FIG. 1A). As illustrated, HCoV-OC43 levels begin to reduce in all three samples when the dose reaches about 30 J/cm$^2$, indicative of the biological effect induced by the 425 nm light and with little or no influence from the associated media and artificial saliva sources.

Figure 1B:
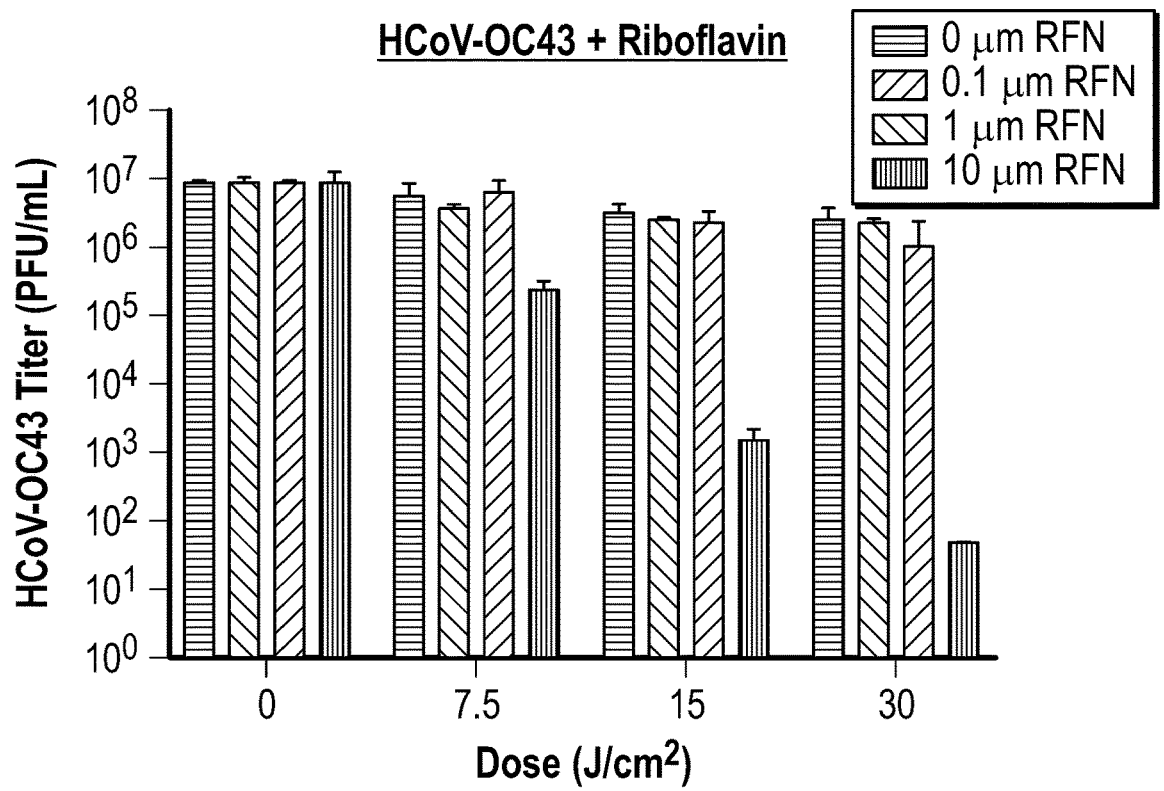
FIG. 1B is a chart illustrating light treatments on HCoV-OC43 samples where various amounts of riboflavin were diluted in artificial saliva and added to the HCoV-OC43 samples.

FIG. 1B is a chart illustrating light treatments on HCoV-OC43 samples where various amounts of riboflavin (abbreviated as RFN) were diluted in a same type of artificial saliva and added to the HCoV-OC43 samples. As illustrated, four HCoV-OC43 samples were prepared including a control sample with no riboflavin (0 µM RFN), and three other samples with different micromolar (µM) concentrations of riboflavin (0.1 µM RFN, 1 µM RFN, and 10 µM RFN). Each of the samples were subjected to 425 nm light at doses up to 45 J/cm$^2$. Compared with the 0 µM RFN sample, the 10 µM RFN exhibited significant decreases in HCoV-OC43, even with doses as low as 7.5 J/cm$^2$. In this manner, light treatments in the presence of riboflavin demonstrate increased efficacy in the inhibition of HCoV-OC43 as compared with the same light treatments without riboflavin, thereby providing effective treatments with reduced light exposure to the associated tissue.

Figure 1C:
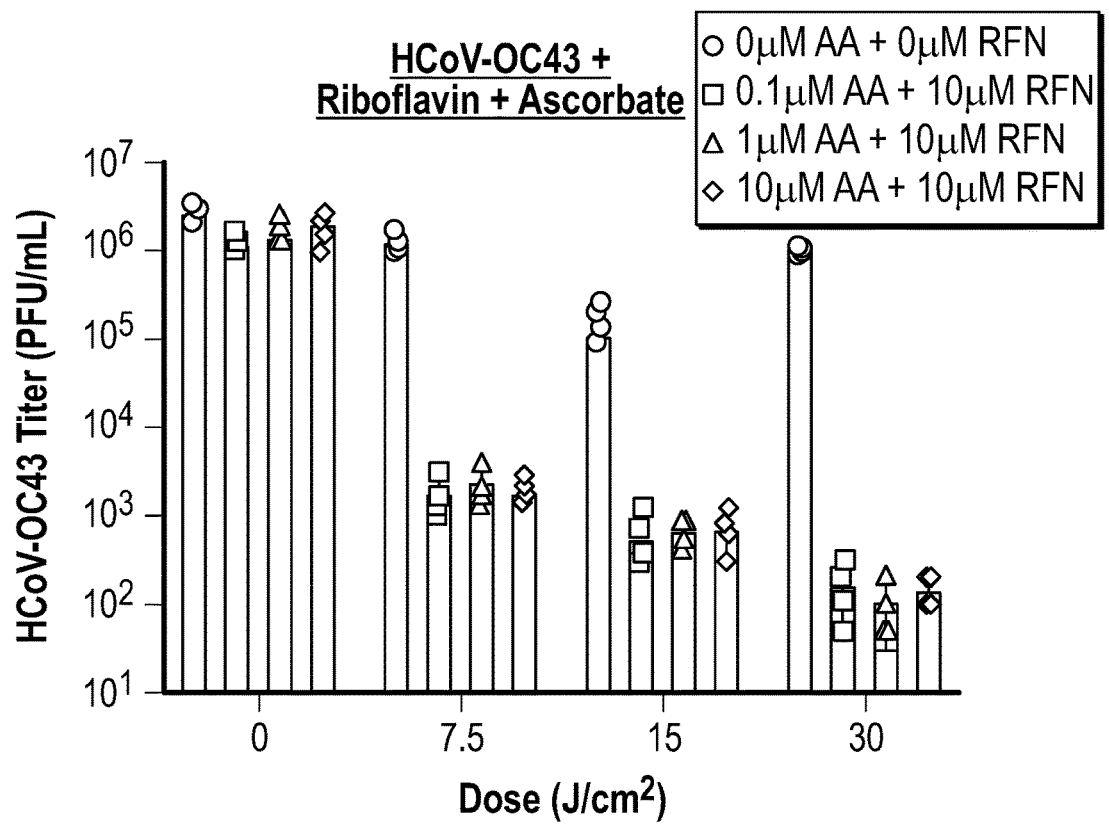
FIG. 1C is a chart illustrating light treatments on HCoV-OC43 samples where various amounts of ascorbate and a common amount of riboflavin were diluted in artificial saliva and added to the HCoV-OC43 samples.

FIG. 1C is a chart illustrating light treatments on HCoV-OC43 samples where various amounts of ascorbate (abbreviated as AA) and 10 µM of RFN were diluted in a same type of artificial saliva and added to the HCoV-OC43 samples. As illustrated, four HCoV-OC43 samples were prepared including a control sample with no ascorbate and no riboflavin (0 µM AA+0 µM RFN), and three other samples with different micromolar concentrations of AA added to 10 µM of RFN (0.1 µM AA+10 µM RFN, 1 µM AA+10 µM RFN, and 10 µM AA+10 µM RFN). The constant amount of RFN (10 µM) was selected based on the improvements illustrated in FIG. 1B. As illustrated in FIG. 1C, all three samples with ascorbate demonstrated even more pronounced reductions in viral loads of HCoV-OC43. Significantly, the lower 7.5 J/cm$^2$ dose of 425 nm light exhibited even greater viral load reduction than the corresponding light dose for the 10 µM RFN sample of FIG. 1B. In this regard, light treatments in the presence of riboflavin and ascorbate demonstrate even further increased efficacy in the inhibition of HCoV-OC43 as compared with the same light treatments with just riboflavin.

Figure 1D:
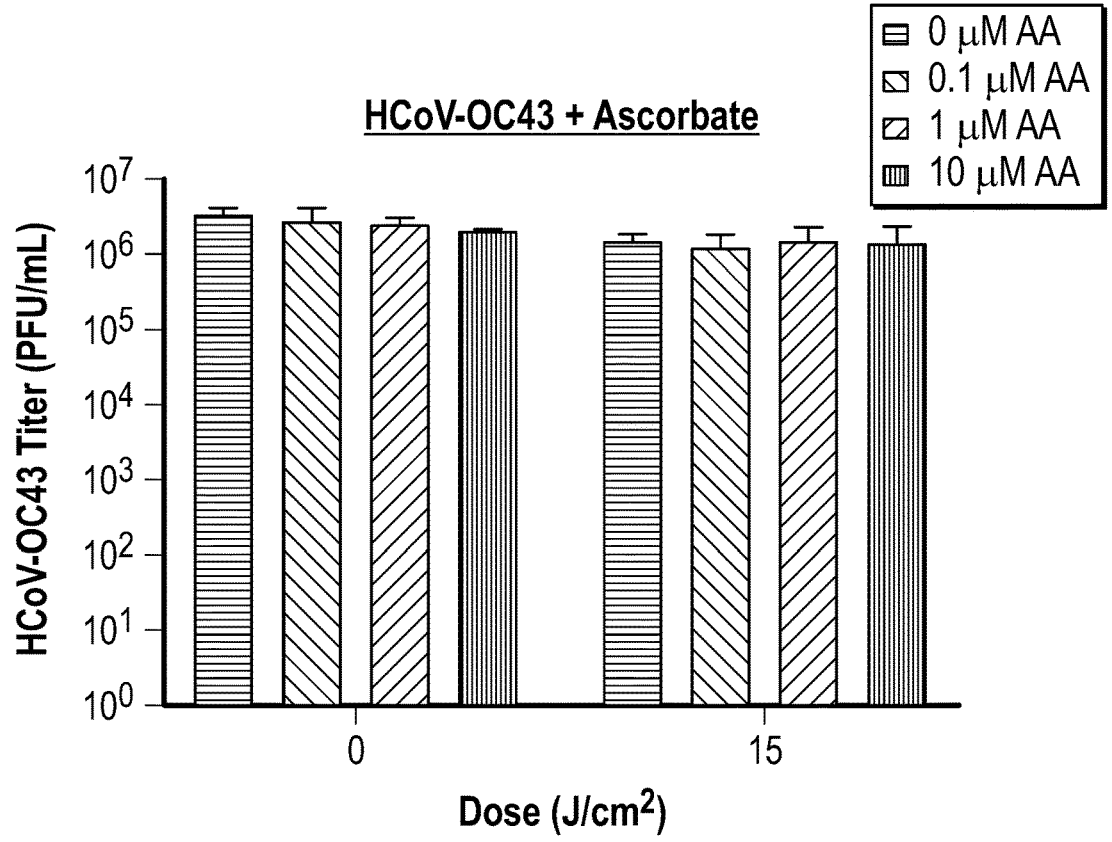
FIG. 1D is a chart illustrating light treatments on HCoV-OC43 samples where various amounts of ascorbate were diluted in artificial saliva and added to the HCoV-OC43 samples in the absence of riboflavin.

FIG. 1D is a chart illustrating light treatments on HCoV-OC43 samples where various amounts of ascorbate were diluted in a same type of artificial saliva and added to the HCoV-OC43 samples in the absence of riboflavin. As illustrated, four HCoV-OC43 samples were prepared including a control sample with no ascorbate (0 µM AA), and three other samples with different micromolar concentrations of ascorbate (0.1 µM AA, 1 µM AA, and 10 µM AA). Each of the samples were subjected to 425 nm light at a dose of 15 J/cm$^2$. As illustrated, ascorbate alone exhibited little to no changes in viral loads of HCoV-OC43 at such dosing.

Taken as a whole, FIGS. 1A to 1D demonstrate that light treatments in the presence of riboflavin show increased efficacy in reducing viral loads of HCoV-OC43. FIGS. 1A to 1D additionally demonstrate that such efficacy may be further increased with the presence of ascorbate, even in low quantities. Accordingly, effective doses of light for treatments of viruses, such as HCoV-OC43, may be reduced when one or more vitamins are present, thereby reducing light exposure to associated tissue.

Figures 2, 3A:
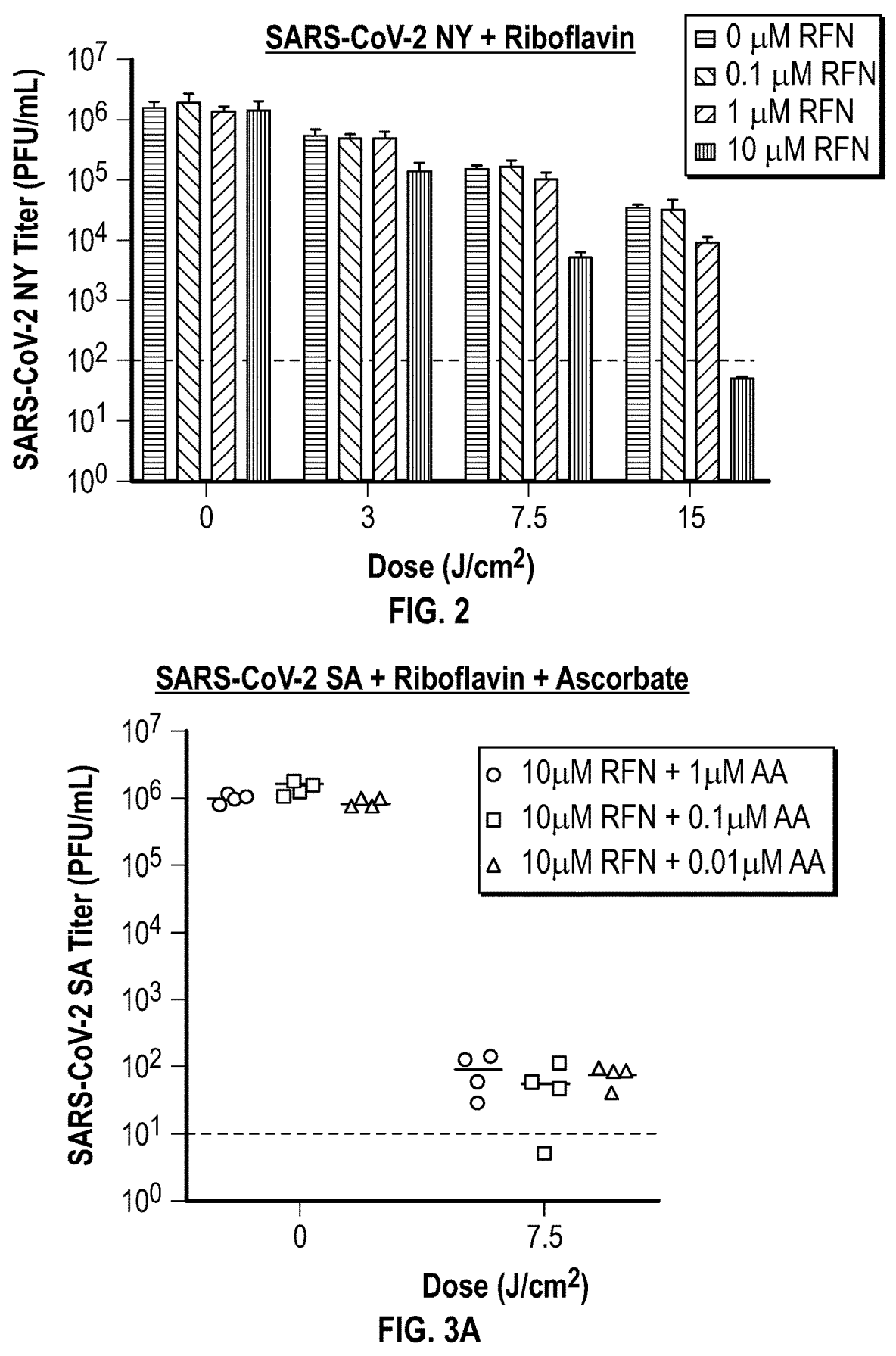

FIG. 2 is a chart illustrating light inhibition of SARS-CoV-2 in the presence of one or more vitamins according to principles of the present disclosure. The SARS-CoV-2 samples were prepared in a media and various quantities of riboflavin in an artificial saliva were added to the samples. For the purposes of this demonstration, the samples were a New York variant of SARS-CoV-2 (or SARS-CoV-2 NY). As illustrated, four SARS-CoV-2 NY samples were prepared including a control sample with no riboflavin (0 µM RFN), and three other samples with different micromolar concentrations of riboflavin (0.1 µM RFN, 1 µM RFN, and 10 µM RFN). Each of the samples were subjected to 425 nm light at doses up to 15 J/cm$^2$. Compared with the 0 µM RFN sample, the 10 µM RFN sample exhibited notable decreases in SARS-CoV-2 NY, beginning with doses as low as 3 J/cm$^2$. Additionally, a dose of 15 J/cm$^2$ reduced the viral load below measurement background levels as indicated by the horizontal dashed line in FIG. 2. In this manner, light treatments in the presence of riboflavin demonstrate increased efficacy in the reduction of viral loads of SARS-CoV-2 NY according to embodiments of the present disclosure.

Figure 3B:
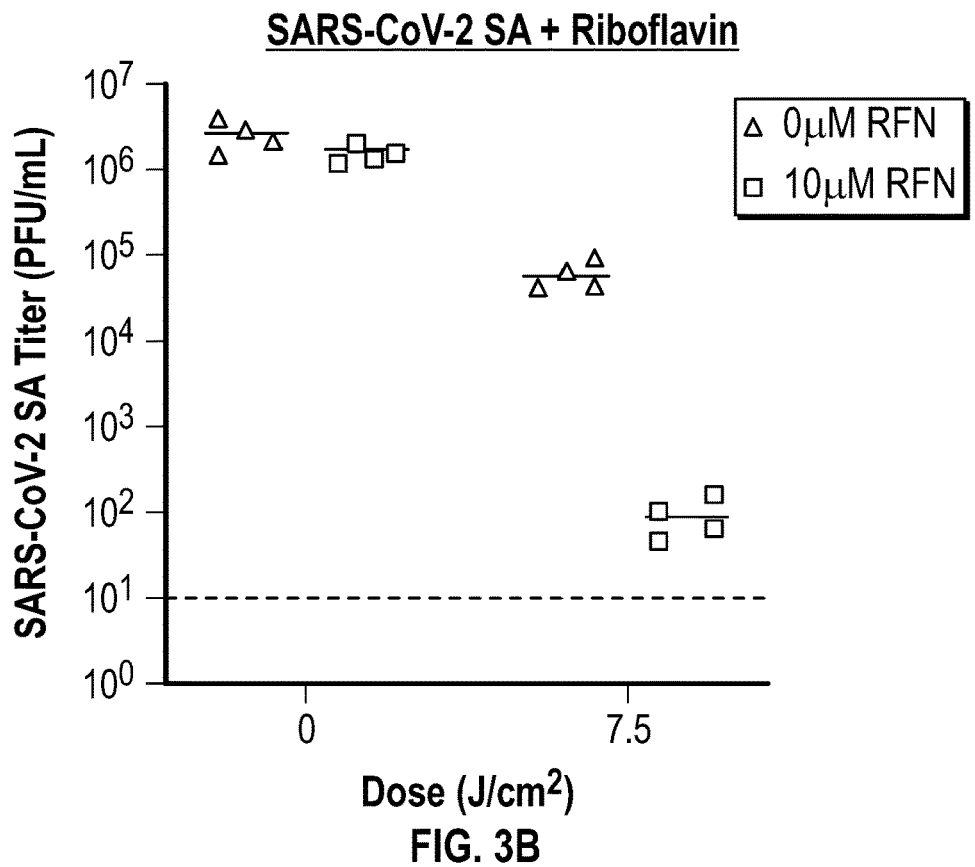
FIG. 3B is a chart illustrating light treatments on SARS-CoV-2 SA samples where various amounts of riboflavin were diluted in a same type of artificial saliva and added to the SARS-CoV-2 SA samples in the absence of ascorbate.
Figure 3C:
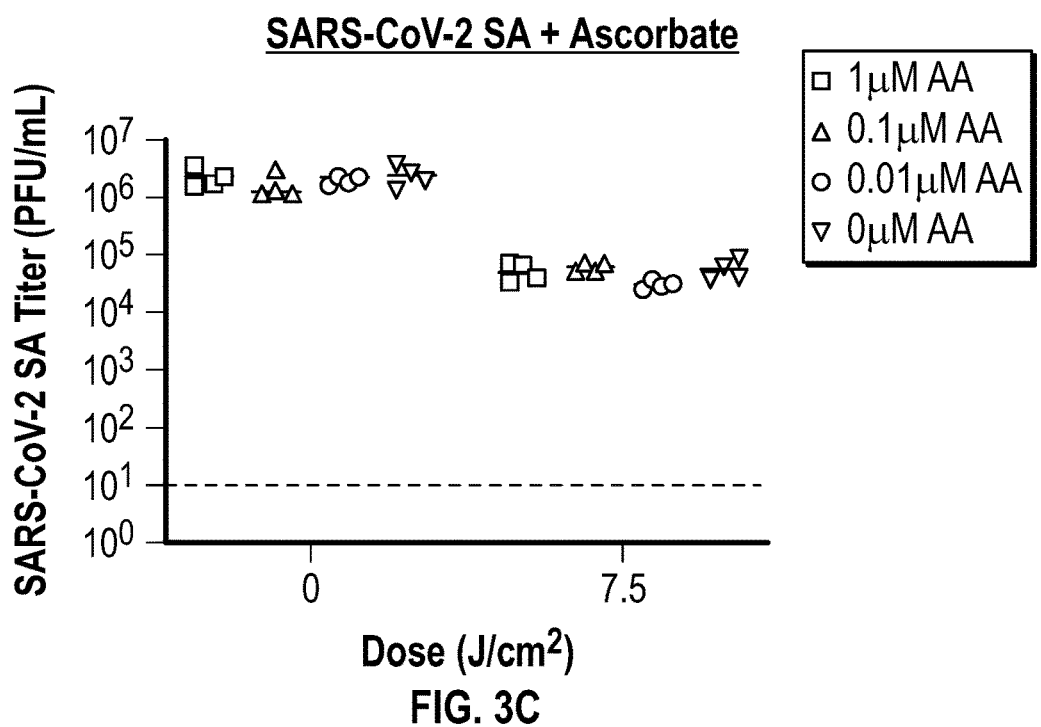
FIG. 3C is a chart illustrating light treatments on SARS-CoV-2 SA samples where various amounts of ascorbate were diluted in a same type of artificial saliva and added to the SARS-CoV-2 SA samples in the absence of riboflavin.
Figure 5A:
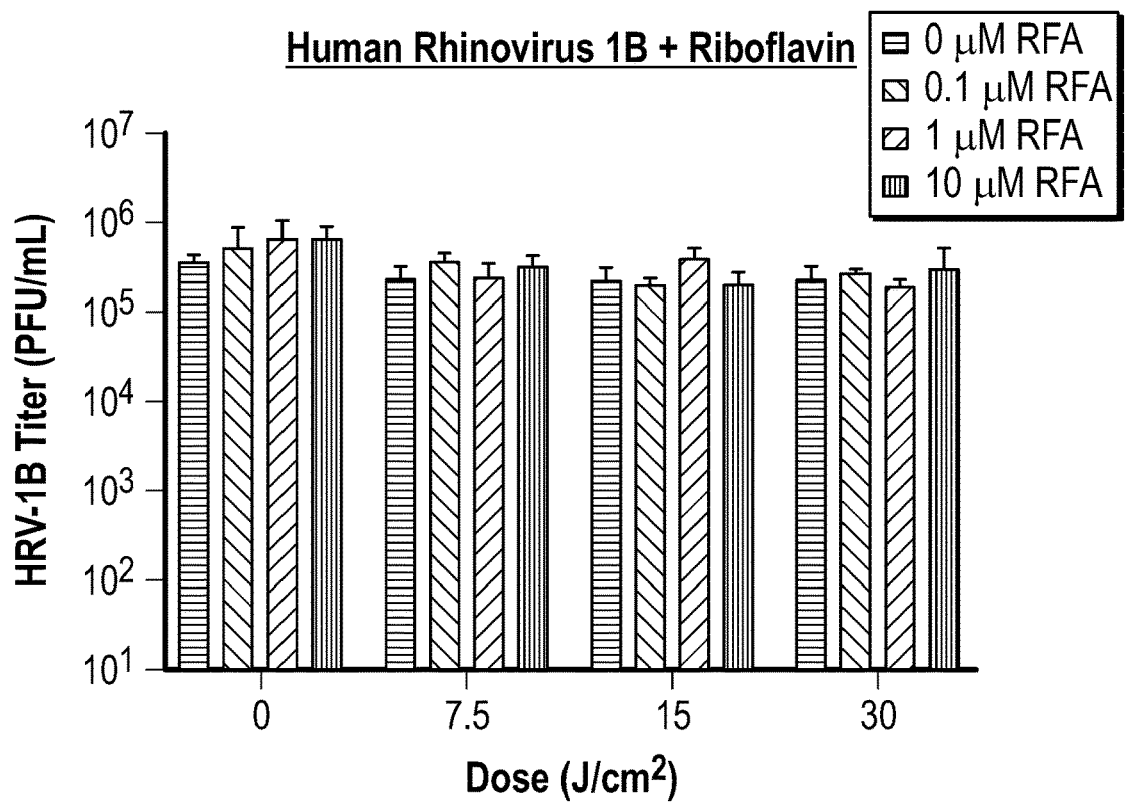
FIG. 5A is a chart illustrating light treatments of human rhinovirus in the presence of one or more vitamins in a first saliva sample.
Figure 5B:
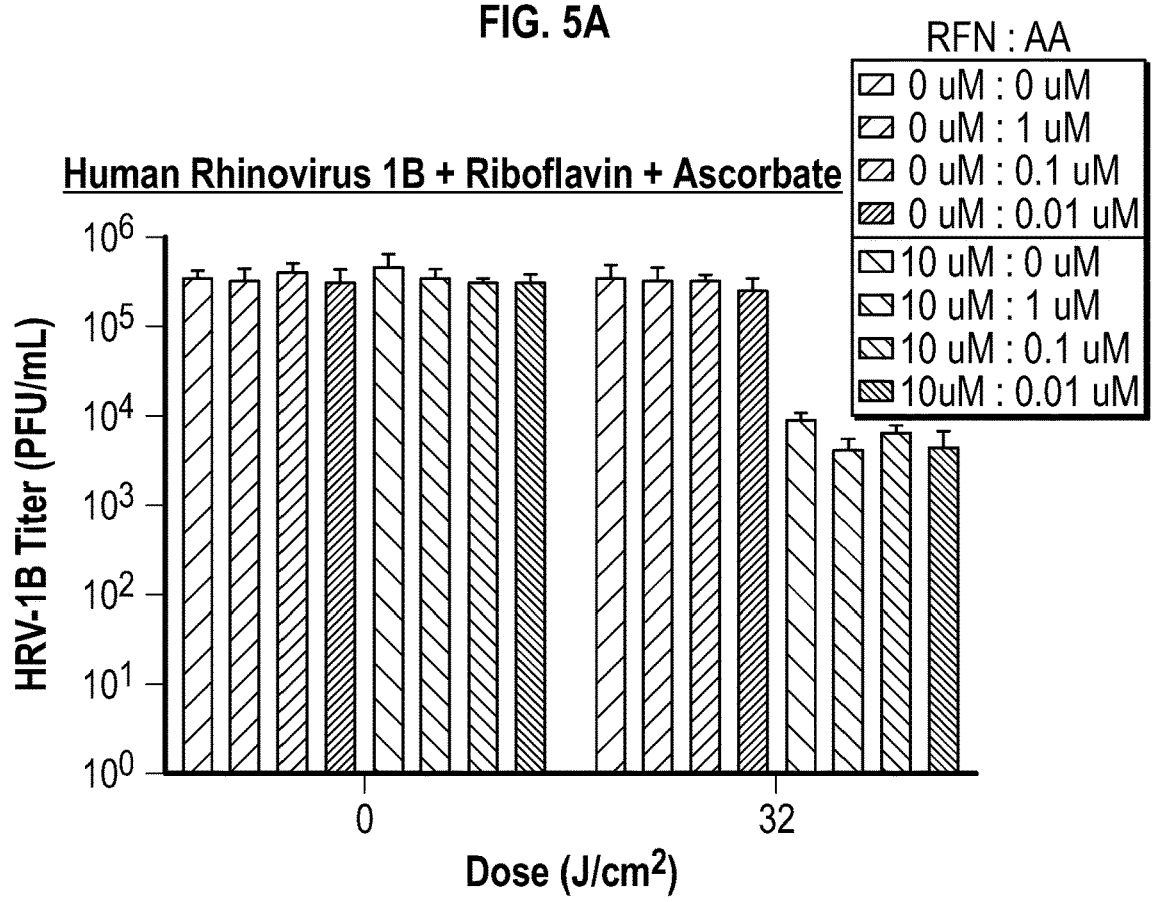
FIG. 5B is a chart illustrating light treatments of human rhinovirus in the presence of one or more vitamins in a second saliva sample.
Figure 6A:
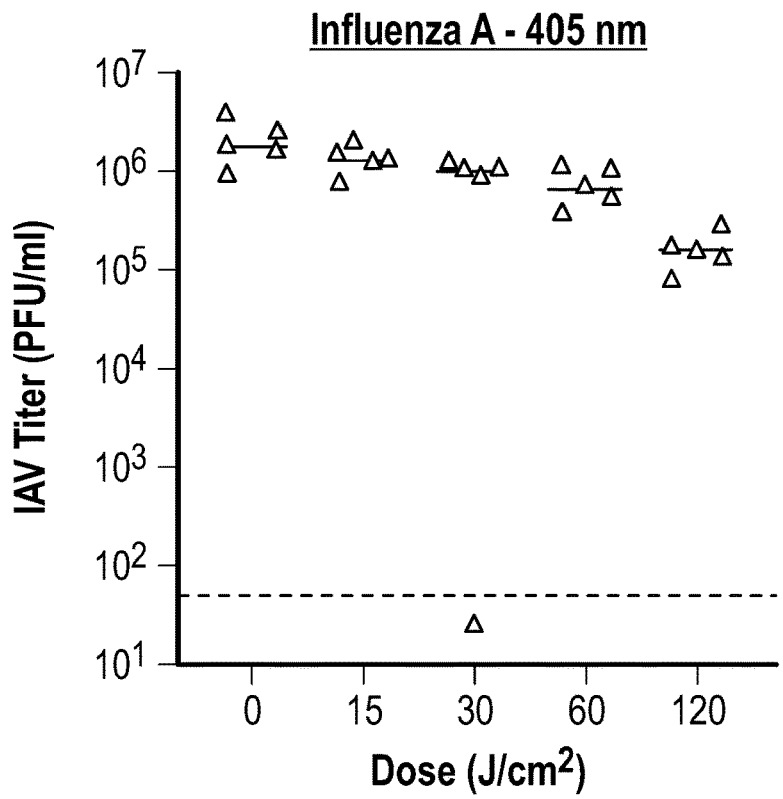
FIG. 6A is a chart illustrating an experimental control where light treatments at 405 nanometers (nm) were applied to influenza A samples in media and in the absence of any vitamins.
Figure 6B:
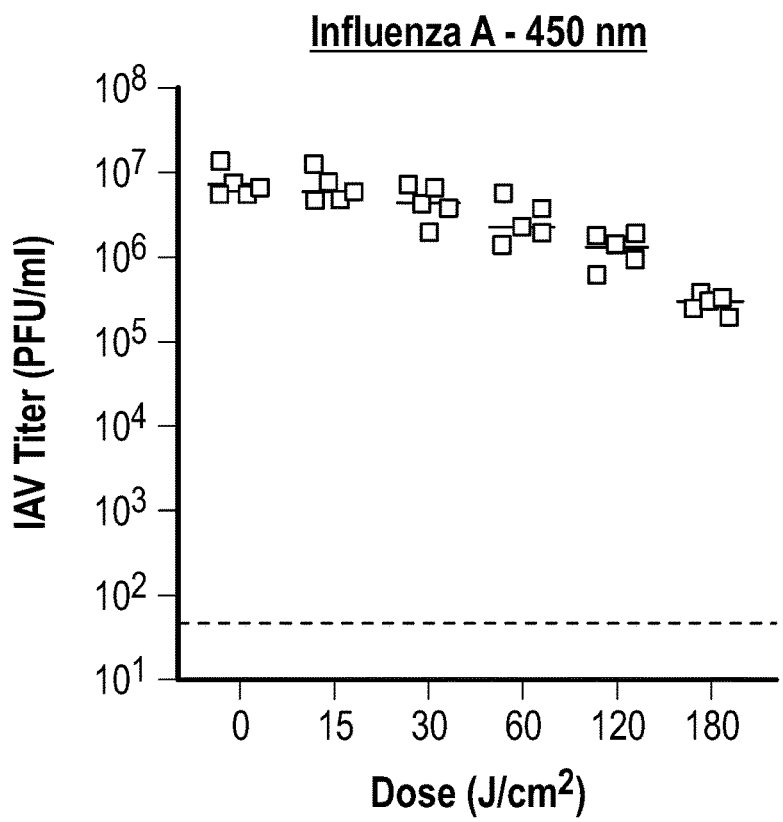
FIG. 6B is a chart illustrating an experimental control where light treatments at 450 nm were applied to influenza A samples in media and in the absence of any vitamins.
Figure 6C:
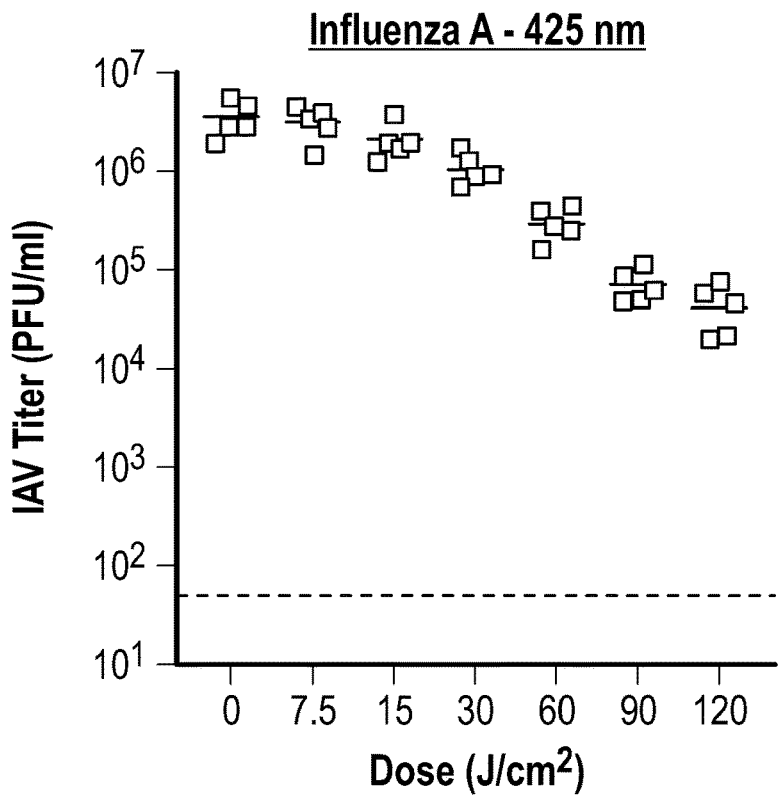
FIG. 6C is a chart illustrating an experimental control where light treatments at 425 nm were applied to influenza A samples in media and in the absence of any vitamins.
Figure 6D:
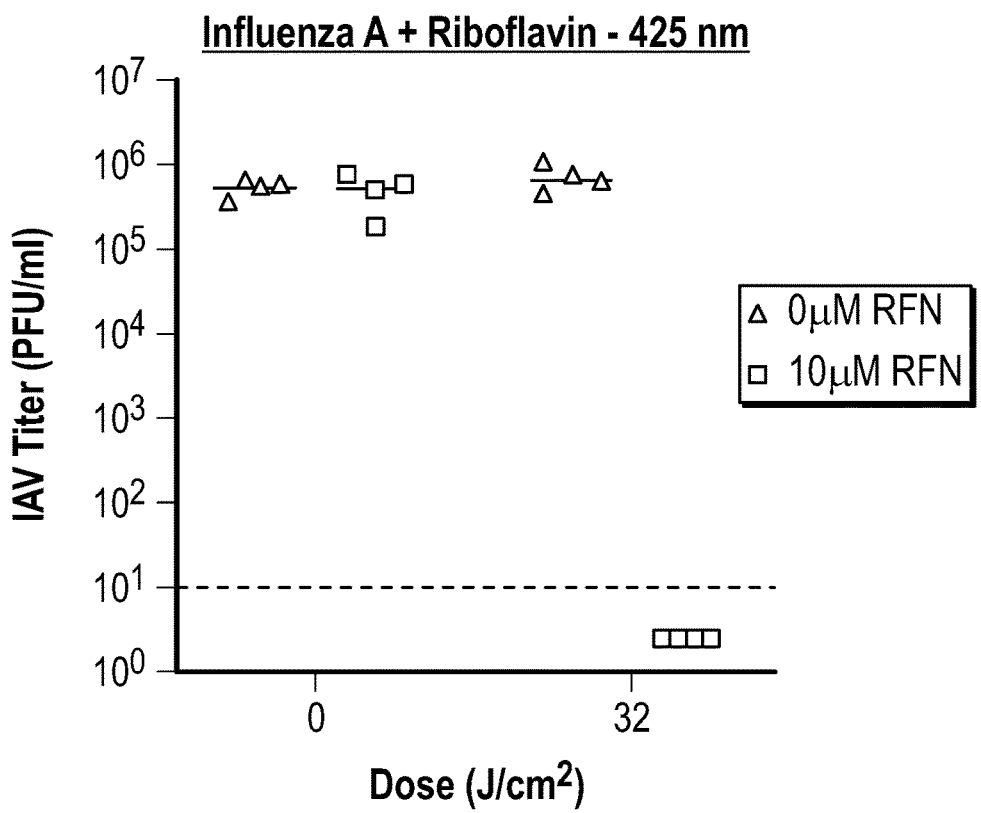
FIG. 6D is a chart illustrating light treatments of influenza A at 425 nm in the presence of one or more vitamins.
Figure 6E:
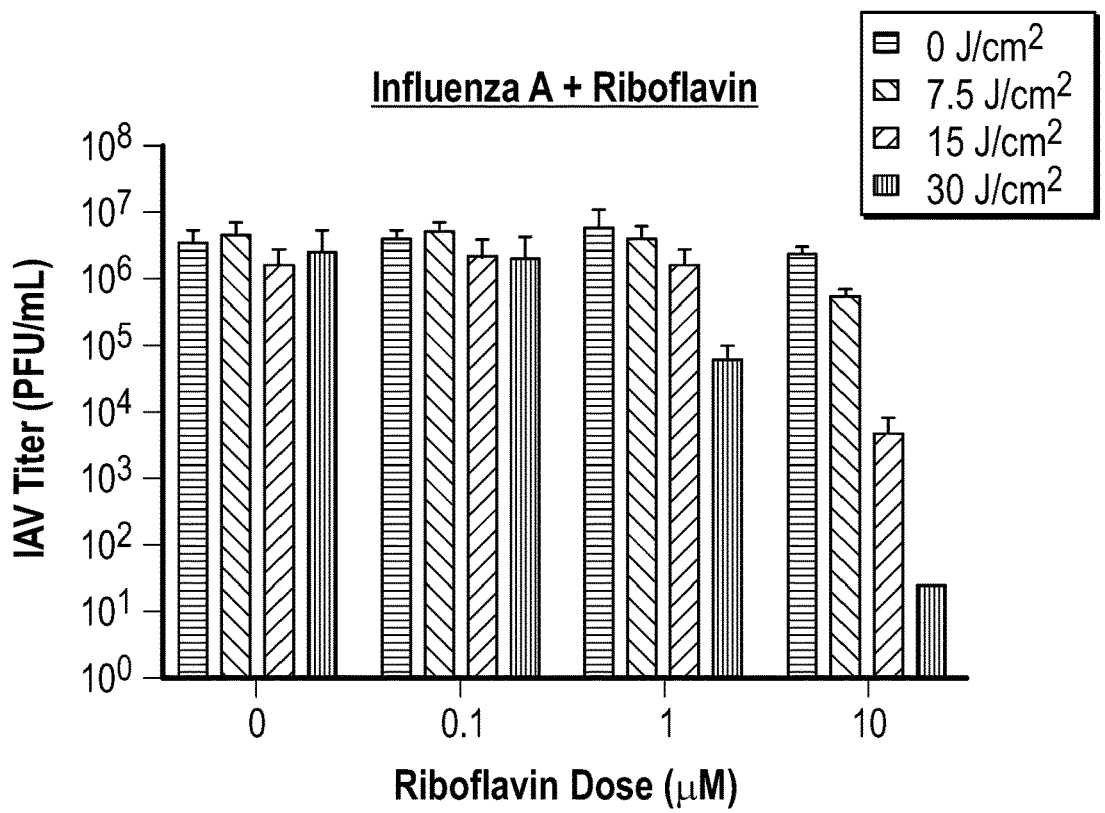
FIG. 6E is another chart illustrating light treatments of influenza A in the presence of one or more vitamins.
Figure 6F:
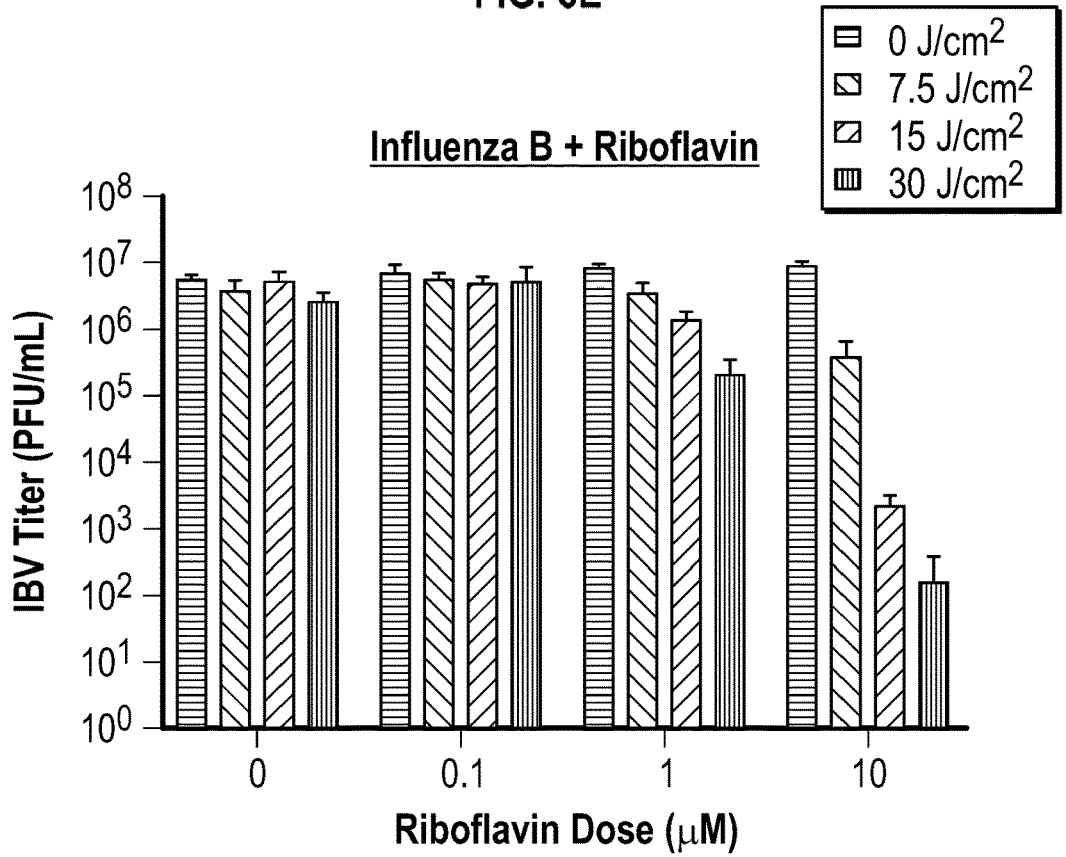
FIG. 6F is a chart illustrating light treatments of influenza B in the presence of one or more vitamins.

FIGS. 3A to 3C are charts illustrating light inhibition of other strains of SARS-CoV-2 in the presence of one or more vitamins according to principles of the present disclosure. The SARS-CoV-2 samples were prepared in a media and various quantities of riboflavin and/or ascorbate in artificial saliva were added to the samples. For the purposes of this demonstration, the samples were the South African variant of SARS-CoV-2 (or SARS-CoV-2 SA) and the 425 nm light was dosed at 7.5 J/cm$^2$.

FIG. 3A is a chart illustrating light treatments on SARS-CoV-2 SA samples where various amounts of ascorbate and 10 micromolar (µM) of riboflavin were diluted in a same type of artificial saliva and added to the SARS-CoV-2 SA samples. As illustrated, three SARS-CoV-2 SA samples were prepared with different micromolar concentrations of ascorbate and 10 µM of riboflavin (10 µM RFN+1 µM AA, 10 µM RFN+0.1 µM AA, and 10 µM RFN+0.01 µM AA). In a manner consistent with the HCoV-OC43 samples of FIG. 1C, combinations of riboflavin and ascorbate demonstrated significant reductions in viral loads of SARS-CoV-2 SA at a relatively low dose of 7.5 J/cm$^2$.

FIG. 3B is a chart illustrating light treatments on SARS-CoV-2 SA samples where various amounts of riboflavin were diluted in a same type of artificial saliva and added to the SARS-CoV-2 SA samples in the absence of ascorbate. As illustrated, a control SARS-CoV-2 SA sample was prepared without riboflavin (0 µM RFN) and another SARS-CoV-2 SA sample was prepared with 10 µM of riboflavin (10 µM RFN). At the 7.5 J/cm$^2$ dose, the 10 µM RFN sample demonstrated significant reductions in viral loads of SARS-CoV-2 SA in a manner similar to FIG. 3A. For example, the 10 µM RFN sample demonstrated about a 99.8% reduction, or a 642-fold reduction, in viral loads of SARS-CoV-2 SA. In comparison, the 10 µM RFN samples for SARS-CoV-2 NY of FIG. 2 demonstrated such decreases at the 15 J/cm$^2$ dose.

FIG. 3C is a chart illustrating light treatments on SARS-CoV-2 SA samples where various amounts of ascorbate were diluted in a same type of artificial saliva and added to the SARS-CoV-2 SA samples in the absence of riboflavin. As illustrated, four SARS-CoV-2 SA samples were prepared including a control sample with no ascorbate (0 µM AA), and three other samples with different micromolar concentrations of ascorbate (1 µM AA, 0.1 µM AA, and 0.01 µM AA). Each of the samples were subjected to 425 nm light at a dose of 7.5 J/cm$^2$. In a manner similar to the HCoV-OC43 samples illustrated in FIG. 1D, ascorbate alone exhibited little to no changes in viral loads of SARS-CoV-2 SA.

FIGS. 4A to 4B are charts illustrating light inhibition of the MERS-CoV variant in the presence of one or more vitamins according to principles of the present disclosure. The MERS-CoV samples were prepared in a media and various quantities of riboflavin and/or ascorbate in artificial saliva were added to the samples. For the purposes of this demonstration, the MERS-CoV samples were subjected to 425 nm light at various doses in the presence of one or more vitamins. FIG. 4A is a chart illustrating an experimental control where light treatments were applied to MERS-CoV samples in media and in the absence of any vitamins. As illustrated, light treatments alone demonstrated increasing reductions in viral load with increasing administered doses. For example, about an 83.6% reduction in viral load was exhibited at the 15 J/cm$^2$ dose. FIG. 4B is a chart illustrating light treatments on MERS-CoV samples where various amounts of ascorbate and 1 µM of riboflavin were diluted in a same type of artificial saliva and added to the MERS-CoV samples. As illustrated, all samples with only 1 µM of riboflavin demonstrated significant reductions (i.e., greater than 99.999% reductions) in viral loads at the 15 J/cm$^2$ dose. The MERS-CoV samples did not show notable differences in amounts of ascorbate. However, a relatively small quantity of riboflavin appears suitable for promoting significant decreases in viral load of MERS-CoV.

With consideration to FIGS. 2 to 4B, light treatments in the presence of riboflavin may demonstrate increased efficacy in reducing viral loads of various strains of SARS-CoV-2 and MERS-CoV. Additionally, FIGS. 3A to 4B demonstrate that such increased efficacy may be related to the presence of riboflavin, while the presence of ascorbate may not have shown further improvements. The differences in response between the HCoV-OC43 samples of FIGS. 1A to 1D and the SARS-CoV-2 and MERS-CoV samples relative to the addition of ascorbate indicates virus specificity between types of vitamins present. In this regard, one or more combinations of vitamins that are present may be tailored based on the specific virus that is targeted. For example, various strains of SARS-CoV-2 or MERS-CoV may only require riboflavin while HCoV-OC43 treatments may show increased benefits with the addition of ascorbate. In further applications, when it may not be known what virus is present, combinations of vitamins (e.g., both riboflavin and ascorbate) may be universally applied to improve efficacy of light treatments in the inhibition of viral loads.

FIG. 5A is a chart illustrating light treatments of human rhinovirus in the presence of one or more vitamins in a first artificial saliva sample. Human rhinovirus is predominantly known as one of the viruses associated with the common cold. For FIG. 5A, human rhinovirus 1B samples were prepared in a media and various quantities of riboflavin in an artificial saliva were added to the samples. In FIG. 5A, the first artificial saliva sample was the same Saliva 1 sample as described for FIG. 1A. As illustrated, four human rhinovirus 1B samples were prepared including a control sample with no riboflavin (0 μM RFN), and three other samples with different micromolar concentrations of riboflavin (0.1 μM RFN, 1 μM RFN, and 10 μM RFN). Each of the samples were subjected to 425 nm light at doses up to 30 J/cm$^2$. As illustrated, the viral loads demonstrated little to no influence with the light treatments, indicating that mechanisms of action for such light treatments may be virus specific.

FIG. 5B is a chart illustrating light treatments of human rhinovirus in the presence of one or more vitamins in a second artificial saliva sample. The second artificial saliva sample was the same Saliva 2 sample as described for FIG. 1A. As illustrated, eight human rhinovirus 1B samples were prepared including a control sample with no riboflavin or ascorbate (0 μM:0 μM-RFN:AA), three samples with various micromolar concentrations (1 μM, 0.1 μM, 0.01 μM) of ascorbate and no riboflavin, and four samples with various micromolar concentrations of ascorbate (1 μM, 0.1 μM, 0.01 μM) and 10 μM riboflavin. Each of the samples were subjected to 425 nm light at doses of 32 J/cm$^2$. Notably, all of the 10 μM riboflavin demonstrated some reduction in viral loads that were not exhibited in the samples of FIG. 5A. In this manner, differences in saliva types may have some influence in human rhinovirus 1B samples.

FIGS. 6A through 6F are charts illustrating light treatments of influenza A and B with and without the presence of one or more vitamins according to principles of the present disclosure. The influenza samples were prepared in a media and various quantities of riboflavin in artificial saliva were added to certain samples. FIGS. 6A-6C represent control light treatments on influenza A samples in media without vitamins. FIG. 6A represents light treatments at 405 nm applied to influenza A samples, FIG. 6B represents light treatments at 450 nm applied to influenza A samples, and FIG. 6C represents light treatments at 425 nm applied to influenza A samples in media. As illustrated, the 405 nm of FIG. 6A and the 450 nm treatments of FIG. 6B demonstrated slight reductions in viral load with increasing administered doses. However, the 425 nm treatment as illustrated in FIG. 6C exhibited improved reductions compared to the 405 nm and 450 nm treatments. In this regard, further experiments on influenza A and B were performed at 425 nm wavelengths as illustrated in FIGS. 6D to 6F. While 425 nm was chosen due to a comparison of FIGS. 6A to 6C, other peak wavelengths of light, including ranges that encompass both 405 nm and 450 nm may also exhibit suitable reductions in viral loads in the presence of vitamins as illustrated in FIGS. 6D to 6F.

FIG. 6D is a chart illustrating light treatments at 425 nm on influenza A samples in the presence of riboflavin. As illustrated, the chart of FIG. 6D includes influenza A samples without riboflavin (0 μM) and influenza A samples with 10 μM riboflavin. At doses of 32 J/cm$^2$, the presence of 10 μM riboflavin exhibited dramatic decreases in viral loads. In FIGS. 6E and 6F, four samples were prepared including a control sample with no riboflavin (0 μM), and three other samples with different micromolar concentrations of riboflavin (0.1 μM, 1 μM, and 10 μM). The samples were then exposed to 425 nm light at doses up to 30 J/cm$^2$. FIG. 6E represents influenza A samples. With consideration to the 0 J/cm$^2$ data set, riboflavin dosing alone may exhibit some inhibition in viral load while the other data sets indicate that various light doses may provide some additional inhibition of influenza A. Notably, at a dose of 30 J/cm$^2$, viral loads exhibit some reduction at 1 μM riboflavin and substantial reduction at 10 μM riboflavin, consistent with the chart of FIG. 6D. FIG. 6F represents influenza B samples. As illustrated, light doses of 15 J/cm$^2$ and 30 J/cm$^2$ show notable reductions in viral load at 1 μM and 10 μM riboflavin. In this regard, the light treatments represented in FIGS. 6E and 6F demonstrated differing efficacy between the influenza B and the influenza A samples, although a combination 10 μM riboflavin and a dose of 30 J/cm$^2$ exhibited dramatic reduction in viral loads for both influenza A and influenza B. While not intending to be bound to a particular theory, differences in efficacy may be a result of interaction with certain surface proteins that are specific to different influenza types.

As described above, efficacy of light treatments to target tissue may be enhanced in the presence of one or more vitamins and the specific vitamin and/or combination of vitamins may be tailored to further enhance efficacy for a specific target virus. For example, riboflavin alone or in combination with ascorbate may be implemented to enhance light treatments for one or more enveloped viruses, such as coronaviridae (e.g., HCoV-OC43, SARS-CoV-2, among others) and influenza. Within enveloped virus types, implementations of riboflavin alone or in combination with ascorbate may exhibit increased efficacy for HCoV-OC43 while riboflavin alone may be sufficient for SARS-CoV-2. Light treatments in the presence of vitamins may be effective according to any number of mechanisms. While not intending to be bound to a particular theory, mechanisms may include interaction with various surface proteins that may be present in particular virus types, perturbation of the genetic material, and creation of reactive oxygen species that may interfere with viral lipid bilayer envelopes.

Exemplary illumination devices and related methods for implementation of light treatments in the presence of one or more vitamins are generally provided in FIGS. 7A to 8B. The illustrated regions in FIGS. 7A to 8B are schematic in nature in order to represent principles of the present disclosure and unless otherwise specified, they are not intended to illustrate the precise shape of a particular region of a device.

FIGS. 7A and 7B are illustrations of an exemplary configuration 10 of an illumination device 12 for delivering light to a body tissue 14 to induce at least one biological effect. The body tissue 14 may represent various mammalian tissues, such as those of the upper and/or lower respiratory tract, including tissues and body cavities that are accessible via the oral cavity and/or intranasal passageways. The body tissue 14 may also represent other mammalian tissues and body cavities, including the skin and the ear canal, among others. As previously described, induced biological effects may include least one of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect.

The illumination device 12 may include a light source 16 operable to irradiate light onto a surface of a treatment area 18 of the body tissue 14. The light source 16 may include one or more light sources such as, without limitation, LEDs, OLEDs, SLDs, lasers, and/or any combinations thereof. In certain embodiments, the light source 16 is configured to emit light with a peak wavelength in a range from 315 nm to 600 nm, or in a range from 315 nm to 450 nm, or in a range from 400 nm to 450 nm. In still further embodiments, the light source 16 may embody a multiple wavelength light source that emits light with at least two different peak wavelengths for inducing at least two different biological effects. For example, a multiple wavelength light source may include a first emitter of the light source 16 that provides light with a first peak wavelength in a range from 315 nm to 600 nm, or in a range from 315 nm to 450 nm, or in a range from 400 nm to 450 nm, and a second emitter of the light source 16 that provides light with a second peak wavelength in a range from 600 to 1600 nm, where the second peak wavelength differs from the first peak wavelength by at least 25 nm.

The illumination device 12 may further include emitter-driving circuitry 20 operable to control output of the light source 16 and one or more sensors 22 operable to sense and/or measure attributes of the illumination device 12, the light source 16 and corresponding light, the treatment area 18, the body tissue 14, and/or the environment within which illumination device 12 operates. In certain embodiments, the emitter-driving circuitry 20 may control an output of the light source 16 based on information collected via the one or more sensors 22. Examples of the one or more sensors 22 include, without limitation, temperature sensors, photo sensors, image sensors, proximity sensors, blood pressure or other pressure sensors, chemical sensors, biosensors (e.g., heart rate sensors, body temperature sensors, sensors that detect the presence or concentration of chemical or biological species, or other conditions), accelerometers, moisture sensors, oximeters, such as pulse oximeters, current sensors, voltage sensors, and the like.

Figure 7A:
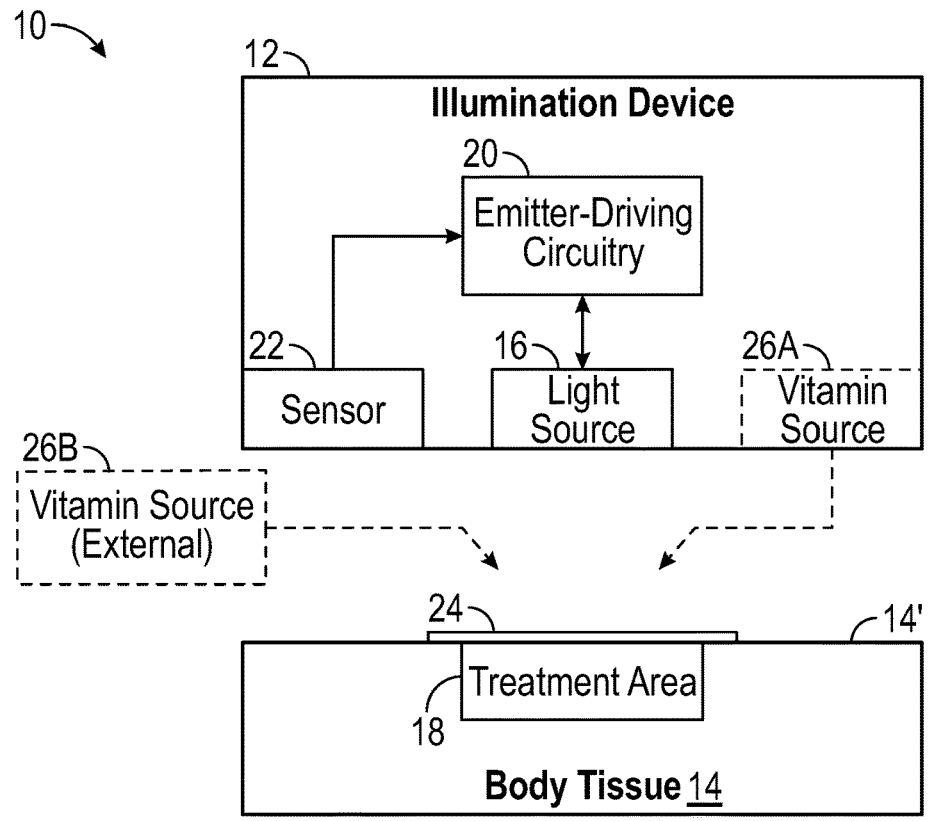
FIG. 7A is an illustration of an exemplary configuration of an illumination device for delivering light to a body tissue in the presence of one or more vitamins to induce at least one biological effect.

As further illustrated in FIG. 7A, a topical coating 24 may first be applied or otherwise formed on a surface 14' of the body tissue 14. The topical coating 24 may be registered with the targeted treatment area 18. In certain embodiments, the topical coating 24 may cover an area of the surface 14' that is greater than the intended treatment area 18 in order to ensure suitable coverage of the treatment area 18. As illustrated, the treatment area 18 may extend from the surface 14' to depth within the body tissue 14. In other embodiments, the treatment area 18 may primarily correspond with the surface 14' of the body tissue 14 or a depth of about 1 mm or less from the surface 14'. The topical coating 24 may comprise one or more vitamins as described above, including but not limited to riboflavin and/or ascorbate, depending on the specific light treatment implementation. The topical coating 24 may further comprise one or more body fluids associated with the body tissue 14, such as saliva for the oral cavity and/or oropharynx and mucus for the upper respiratory tract.

The one or more vitamins may be provided by a vitamin source 26A that is incorporated within the illumination device 12 and/or by a vitamin source 26B that is external to the illumination device 12. The vitamin sources 26A, 26B may comprise one or more vitamins that are provided in the form of a solution that may be sprayed, swallowed, or otherwise applied to form the topical coating 24. Examples of external vitamin sources 26B include liquids that may be sprayed, dispensed, and/or swallowed to the treatment area 18. In other embodiments specific to the oral cavity and oropharynx, the external vitamin source 26B may be provided in the form of an oral dose that may be chewed and swallowed, such as a chewable tablet or a chewable gummy. In the example where the vitamin source 26A is incorporated with the illumination device 12, the vitamin source 26A may embody a filled reservoir of the illumination device 12 where the one or more vitamins may be sprayed or dispensed on the treatment area 18. Incorporating the vitamin source 26A with the illumination device 12 may advantageously align the light source 16 and the vitamin source 26A in a concurrent manner relative to the treatment area 18.

Figure 7B:
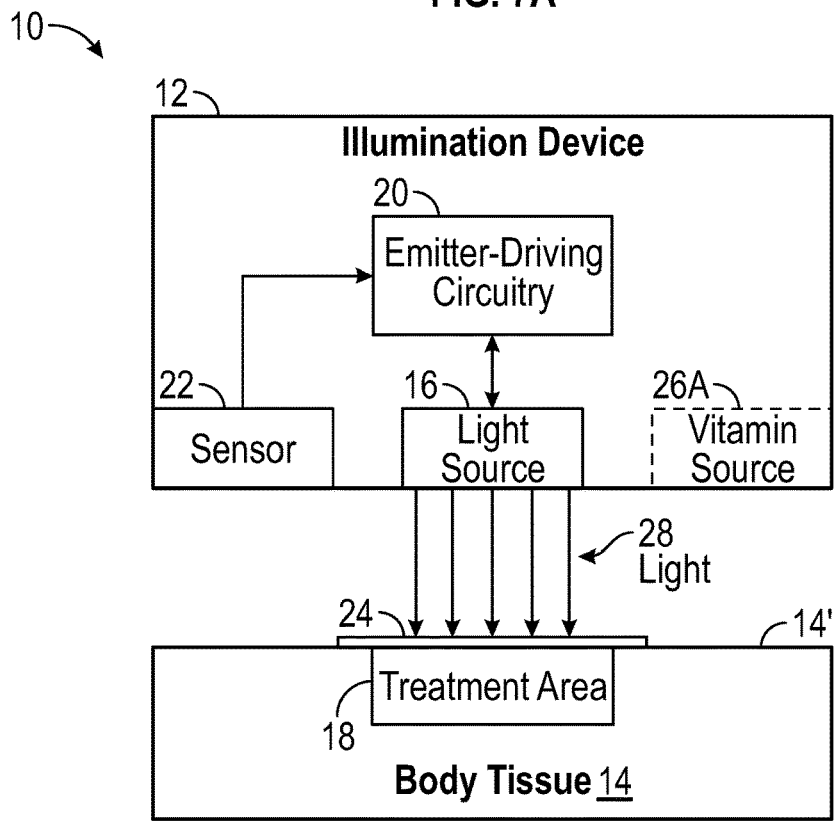
FIG. 7B is an illustration of the exemplary configuration of FIG. 7A showing delivery of the light to the body tissue after a topical coating that includes the one or more vitamins is applied to the body tissue.

As illustrated in FIG. 7B, the light source 16 may be electrically activated to emit light 28 and irradiate the treatment area 18 after the topical coating 24 is formed. In certain embodiments, the light source 16 may be positioned so that one or more portions of the light 28 impinge the treatment area 18 with an angle of incidence of 90 degrees with a tolerance of plus or minus 10 degrees, although other angles of incidence may also be employed. The light source 16 may also be configured to provide a beam uniformity of the light 28 of no more than about 20%, or no more than about 15%, or no more than about 10% of a range over mean at the treatment area 18. Such beam uniformity values may be determined based on selection of optics and/or waveguides for directing the light 28 from the light source 16. In certain embodiments, the light source 16 may be capable of providing an irradiance to the treatment area 18 of up to about 45 mW/cm$^2$ when positioned at a distance of about 96 mm from the treatment area 18, or up to about 60 mW/cm$^2$ when positioned at a distance of about 83 mm from the treatment area 18, or up to about 80 mW/cm$^2$ when positioned at a distance of about 70 mm from the treatment area 18. In the case of the oropharynx, such distances may be measured from the incisors of user to the oropharynx. The above angles of incidence, beam uniformity, and irradiance values are provided as examples. In practice, such values may be configured in other ranges based on the application.

FIGS. 8A and 8B are illustrations of another exemplary configuration 30 of an illumination device 12 that includes a light guide 32 for delivering light to the body tissue 14 to induce at least one biological effect. In certain applications, the light guide 32 may be configured such that at least a portion of the light guide 32 may be positioned within a body cavity 34 of a user to target the treatment area 18. For example, the body cavity 34 may be an oral cavity, and the light guide 32 may be shaped to fit through a mouth and the treatment area 18 may correspond with tissue within the oral cavity and/or the oropharynx. In various other embodiments, the light guide 32 may be suitably shaped based on the body cavity 34 it will be inserted into. For example, the light guide 32 may be shaped to conform to or fit within at least one of an oral cavity, a nasal cavity, an ear cavity, a throat cavity, a laryngeal cavity, a pharyngeal cavity, a tracheal cavity, an esophageal cavity, a urethral cavity, a vaginal cavity, or a cervical cavity.

The light guide 32 may embody any light delivery component, such as fiber optic, a solid waveguide, a hollow waveguide, and the like that is configured to deliver light to the treatment area 18. The light guide 32 may be constructed from a thermally and/or electrically insulating material. In certain embodiments, the light guide 32 may comprise one or more of glass, polycarbonate, a metal encased tube, or even silicone. The light guide 32 may comprise a rigid material that at least partially displaces some tissue of the body cavity 34 to target the treatment area 18 or the light guide 32 may comprise a flexible material that conforms to a shape of the body cavity 34 to target the treatment area 18. In certain embodiments, the light guide 32 may embody light-blocking outer walls so that light may target the treatment area 18 and avoid other protected areas 36 within the body cavity 34. As illustrated, the light source 16 may be positioned such that the light guide is optically coupled to the light source 16 in order to provide light into the light guide 32. Additionally, for embodiments where the vitamin source 26A is incorporated with the illumination device 12, the light guide 32 may further serve to direct the one or more vitamins to the treatment area 18 to form the topical coating 24. This is represented in FIG. 8A by the dashed line with end arrow illustrated within a hollow opening or core of the light guide 32.

As illustrated in FIG. 8B, the light source 16 may be electrically activated to emit light 28 and irradiate the treatment area 18 within the body cavity 34 after the topical coating 24 is formed. In certain embodiments, the light guide 32 may be shaped to allow the light 28 to travel along a direct path 28' to the treatment area 18 within the body cavity 34 while also reducing amounts of the light 28 that would otherwise travel along a now blocked path 28" to the protected area 36.

It is contemplated that any of the foregoing aspects, and/or various separate aspects and features as described herein, may be combined for additional advantage. Any of the various embodiments as disclosed herein may be combined with one or more other disclosed embodiments unless indicated to the contrary herein.

Those skilled in the art will recognize improvements and modifications to the preferred embodiments of the present disclosure. All such improvements and modifications are considered within the scope of the concepts disclosed herein and the claims that follow.

What is claimed is:

1. A method comprising:
   providing a topical coating to a surface of mammalian tissue, the topical coating comprising at least one vitamin;
   providing a light source configured to emit light; and
   irradiating the surface of the mammalian tissue with the light to induce a biological effect, wherein the topical coating and the light are provided through a same light delivery element, the light delivery element being configured to provide a direct path for at least a portion of light to travel between the light source and the mammalian tissue without internal reflections.

2. The method of claim 1, wherein the at least one vitamin comprises a source of riboflavin.

3. The method of claim 1, wherein the at least one vitamin comprises a source of riboflavin and a source of ascorbate.

4. The method of claim 1, wherein providing the topical coating comprises applying a solution to the surface of the mammalian tissue, wherein the solution comprises the at least one vitamin.

5. The method of claim 1, wherein the topical coating comprises a mixture of a bodily fluid and the at least one vitamin.

6. The method of claim 5, wherein the bodily fluid comprises saliva.

7. The method of claim 5, wherein the bodily fluid comprises mucus.

8. The method of claim 1, wherein the light source is configured to emit light with a peak wavelength in a range from 315 nm to 600 nm.

9. The method of claim 1, wherein the light source is configured to emit light with a peak wavelength in a range from 400 nm to 450 nm.

10. The method of claim 1, wherein the light source is configured to emit light with a first peak wavelength in a range from 315 nm to 600 nm and a second peak wavelength in a range from 600 nm to 1600 nm, wherein the first peak wavelength is different than the second peak wavelength.

11. The method of claim 1, wherein the biological effect comprises altering a concentration of one or more pathogens and altering growth of the one or more pathogens.

12. The method of claim 11, wherein the one or more pathogens comprise an enveloped virus.

13. The method of claim 12, wherein the enveloped virus comprises coronaviridae.

14. The method of claim 12, wherein the enveloped virus comprises influenza.

15. The method of claim 1, wherein the light delivery element comprises a light guide.

16. The method of claim 15, wherein the mammalian tissue resides within a body cavity and the light guide is at least partially inserted within the body cavity for irradiating the surface of the mammalian tissue.

17. The method of claim 16, wherein the light guide at least partially displaces a portion of the body cavity to direct the topical coating and the light to the surface of the mammalian tissue.

18. The method of claim 16, wherein the light guide forms the direct path for light to travel through the body cavity to the surface of the mammalian tissue.

19. The method of claim 15, wherein the light guide comprises a hollow core.

20. The method of claim 19, wherein the topical coating is provided through the hollow core to the surface of the mammalian tissue before the light is provided through the hollow core to the mammalian tissue.

21. The method of claim 15, wherein the light guide comprises light-blocking outer walls.

* * * * *